US007645573B2

(12) United States Patent
Ivey et al.

(10) Patent No.: US 7,645,573 B2
(45) Date of Patent: Jan. 12, 2010

(54) DIAGNOSIS OF SEPSIS OR SIRS USING BIOMARKER PROFILES

(75) Inventors: Richard M. Ivey, Parkton, MD (US); Thomas M. Gentle, Jr., Red Lion, PA (US); Richard L. Moore, Glenville, PA (US); Michael L. Towns, Timonium, MD (US); Nicholas Bachur, Jr., Monkton, MD (US); Robert W. Rosenstein, Ellicott City, MD (US); Paul E. Goldenbaum, Hampstead, MD (US); Song Shi, Reisterstown, MD (US); Donald Copertino, Catonsville, MD (US); James Garrett, Baltimore, MD (US); Gregory Tice, Lutherville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 310 days.

(21) Appl. No.: 10/704,666

(22) Filed: Nov. 12, 2003

(65) Prior Publication Data

US 2004/0106142 A1 Jun. 3, 2004

Related U.S. Application Data

(60) Provisional application No. 60/425,322, filed on Nov. 12, 2002.

(51) Int. Cl.
*C12Q 1/68* (2006.01)
*C12P 19/34* (2006.01)
(52) U.S. Cl. .......................... 435/6; 435/91.2
(58) Field of Classification Search .................. None
See application file for complete search history.

(56) References Cited

U.S. PATENT DOCUMENTS

| 5,426,181 | A | 6/1995 | Lee et al. |
| 5,484,705 | A | 1/1996 | White et al. |
| 5,639,617 | A | 6/1997 | Bohuon |
| 5,780,237 | A | 7/1998 | Bursten et al. |
| 5,804,367 | A | 9/1998 | White et al. |
| 5,804,370 | A | 9/1998 | Romaschin et al. |
| 5,830,679 | A | 11/1998 | Bianchi et al. |
| 5,981,180 | A | 11/1999 | Chandler et al. |
| 6,077,665 | A | 6/2000 | Weirich et al. |
| 6,159,683 | A | 12/2000 | Romashin et al. |
| 6,190,872 | B1 | 2/2001 | Slotman |
| 6,251,598 | B1 | 6/2001 | di Giovine et al. |
| 6,268,222 | B1 | 7/2001 | Chandler et al. |
| 6,303,321 | B1 | 10/2001 | Tracey et al. |
| 6,316,199 | B1 | 11/2001 | Vockley et al. |
| 6,420,526 | B1 | 7/2002 | Ruben et al. |
| 6,534,648 | B1 | 3/2003 | Pardy et al. |
| 6,579,719 | B1 | 6/2003 | Hutchens et al. |
| 6,592,822 | B1 | 7/2003 | Chandler |
| 6,599,331 | B2 | 7/2003 | Chandler et al. |
| 6,675,104 | B2 | 1/2004 | Paulse et al. |
| 6,692,916 | B2 | 2/2004 | Bevilacqua et al. |
| 6,872,541 | B2 | 3/2005 | Mills |
| 6,960,439 | B2 | 11/2005 | Bevilacqua et al. |
| 6,964,850 | B2 | 11/2005 | Bevilacqua et al. |
| 2001/0051344 | A1 * | 12/2001 | Shalon et al. .................. 435/6 |
| 2002/0019704 | A1 | 2/2002 | Tusher et al. |
| 2002/0119554 | A1 | 8/2002 | Vockley et al. |
| 2002/0150534 | A1 | 10/2002 | Yu et al. |
| 2003/0004402 | A1 | 1/2003 | Hitt et al. |
| 2003/0027176 | A1 | 2/2003 | Dailey |
| 2003/0044790 | A1 | 3/2003 | Das et al. |
| 2003/0049851 | A1 | 3/2003 | Toh et al. |
| 2003/0057106 | A1 | 3/2003 | Shen et al. |

(Continued)

FOREIGN PATENT DOCUMENTS

EP 1 355 158 A1 10/2003

(Continued)

OTHER PUBLICATIONS

Hoshikawa Y et al 'Hypoxia induces different genes in the lungs of rats compared with mice.' Physiol Genomics. Feb. 6, 2003;12(3):209-19.*
Cheung VG et al 'Natural variation in human gene expression assessed in lymphoblastoid cells.' Nat Genet. Mar. 2003;33(3):422-5.*
Chan E 'Integrating transcriptomics and proteomics.' Genomics & Proteomics, available online from www.genpromag.com, pp. 1-5.*
Thisted R.A. 'What is a P-value?' May 1998, available from http://www.stat.uchicago.edu/~thisted/ pritned pp. 1-6.*

(Continued)

*Primary Examiner*—Stephen Kapushoc
(74) *Attorney, Agent, or Firm*—Jones Day

(57) ABSTRACT

The early prediction or diagnosis of sepsis advantageously allows for clinical intervention before the disease rapidly progresses beyond initial stages to the more severe stages, such as severe sepsis or septic shock, which are associated with high mortality. Early prediction or diagnosis is accomplished using a molecular diagnostics approach, involving comparing an individual's profile of biomarker expression to profiles obtained from one or more control, or reference, populations, which may include a population who develops sepsis. Recognition of features in the individual's biomarker profile that are characteristic of the onset of sepsis allows a clinician to diagnose the onset of sepsis from a bodily fluid isolated at the individual at a single point in time. The necessity of monitoring the patient over a period of time is, therefore, avoided, advantageously allowing clinical intervention before the onset of serious symptoms. Further, because the biomarker expression is assayed for its profile, identification of the particular biomarkers is unnecessary. The comparison of an individual's biomarker profile to biomarker profiles of appropriate reference populations likewise can be used to diagnose SIRS in the individual.

27 Claims, 2 Drawing Sheets

U.S. PATENT DOCUMENTS

| | | |
|---|---|---|
| 2003/0059937 A1 | 3/2003 | Ruben et al. |
| 2003/0087285 A1 | 5/2003 | Chow et al. |
| 2003/0091565 A1 | 5/2003 | Beltzer et al. |
| 2003/0100122 A1 | 5/2003 | Heinecke et al. |
| 2003/0165919 A1 | 9/2003 | Schmitz et al. |
| 2003/0194752 A1 | 10/2003 | Anderson et al. |
| 2003/0219771 A1 | 11/2003 | Bevilacqua et al. |
| 2003/0223996 A1 | 12/2003 | Ruben et al. |
| 2003/0228625 A1 | 12/2003 | Toh et al. |
| 2003/0229455 A1 | 12/2003 | Bevilacqua et al. |
| 2004/0009503 A1 | 1/2004 | Fu et al. |
| 2004/0038201 A1 | 2/2004 | Nau et al. |
| 2004/0072237 A1 | 4/2004 | Schweitzer |
| 2004/0096917 A1 | 5/2004 | Ivey et al. |
| 2004/0097460 A1 | 5/2004 | Ivey et al. |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0133352 A1 | 7/2004 | Bevilacqua et al. |
| 2004/0157242 A1 | 8/2004 | Ivey et al. |
| 2004/0175754 A1 | 9/2004 | Bar-Or et al. |
| 2004/0219568 A1 | 11/2004 | Bevilacqua et al. |
| 2004/0225447 A1 | 11/2004 | Bevilacqua et al. |
| 2004/0225449 A1 | 11/2004 | Bevilacqua et al. |
| 2004/0253637 A1 | 12/2004 | Buechler et al. |
| 2004/0259090 A1 | 12/2004 | Zipfel et al. |
| 2005/0037344 A1* | 2/2005 | Stuhlmuller et al. ........... 435/6 |
| 2005/0060101 A1 | 3/2005 | Bevilacqua et al. |
| 2005/0079490 A1 | 4/2005 | Stuber et al. |
| 2005/0148029 A1 | 7/2005 | Buechler et al. |
| 2005/0164238 A1 | 7/2005 | Valkirs et al. |
| 2005/0196817 A1 | 9/2005 | Kingsmore et al. |
| 2005/0239150 A1 | 10/2005 | Bergmann |
| 2005/0249724 A1 | 11/2005 | Lihme et al. |
| 2005/0250148 A1 | 11/2005 | Bevilacqua et al. |
| 2006/0024744 A1 | 2/2006 | Mills et al. |
| 2006/0062789 A1 | 3/2006 | Ruben et al. |
| 2006/0127912 A1 | 6/2006 | Pachot |
| 2006/0246495 A1* | 11/2006 | Garrett et al. .................. 435/6 |

FOREIGN PATENT DOCUMENTS

| | | |
|---|---|---|
| EP | 1 355 159 A1 | 10/2003 |
| EP | 1 369 693 A1 | 12/2003 |
| RU | 1504597 | 9/1993 |
| RU | 2072103 | 8/1997 |
| WO | WO 94/28418 | 12/1994 |
| WO | WO 95/20163 | 7/1995 |
| WO | WO 96/41291 | 12/1996 |
| WO | WO 98/01738 | 1/1998 |
| WO | WO99/20756 | 4/1999 |
| WO | WO 00/42222 | 7/2000 |
| WO | WO 00/46603 | 8/2000 |
| WO | WO 01/04630 | 1/2001 |
| WO | WO 01/63280 | 8/2001 |
| WO | WO 01/96864 A2 | 12/2001 |
| WO | WO 02/42733 A2 | 5/2002 |
| WO | WO 02/058721 | 8/2002 |
| WO | WO 02/088744 | 11/2002 |
| WO | WO 02/088747 A2 | 11/2002 |
| WO | WO 03/040404 A1 | 5/2003 |
| WO | WO 03/048776 A1 | 6/2003 |
| WO | WO 03/048777 A1 | 6/2003 |
| WO | WO 03/048778 A1 | 6/2003 |
| WO | WO 03/048782 A1 | 6/2003 |
| WO | WO 03/073099 A1 | 9/2003 |
| WO | WO 03/084388 | 10/2003 |
| WO | WO 2004/005539 A1 | 1/2004 |
| WO | WO2004/008138 | 1/2004 |
| WO | WO 2004/043223 | 5/2004 |
| WO | WO 2004/053148 A1 | 6/2004 |
| WO | WO 2004/053155 A1 | 6/2004 |
| WO | WO 2004/053457 A2 | 6/2004 |
| WO | WO 2004/057034 | 7/2004 |
| WO | WO 2004/059293 A2 | 7/2004 |
| WO | WO 2004/087949 A2 | 10/2004 |
| WO | WO 2004/086043 | 11/2004 |
| WO | WO 2004/108957 A2 | 12/2004 |
| WO | WO 2005/033327 A2 | 4/2005 |
| WO | WO 2005/048823 | 6/2005 |
| WO | WO 2005/064307 A2 | 7/2005 |
| WO | WO2005/065015 | 7/2005 |
| WO | WO2006/077471 | 7/2006 |
| WO | WO2006/102408 | 9/2006 |
| WO | WO2006/113529 | 10/2006 |

OTHER PUBLICATIONS

GenBank Locus NM_001966, *Homo sapiens* enoyl-Coenzyme A, hydratase/3-hydroxyacyl Coenzyme A dehydrogenase (EHHADH), mRNA. from www.ncbi.nlm.nih.gov, 4 printed pages.*

GenBank Locus NM_004139, *Homo sapiens* lipopolysaccharide binding protein (LBP), mRNA. from www.ncbi.nlm.nih.gov, 7 printed pages.*

Co-pending U.S. Appl. No. 10/704,758, Ivey et al.

Co-pending U.S. Appl. No. 10/704,899, Ivey et al.

Co-pending U.S. Appl. No. 10/704,661, Ivey et al.

Van Leeuwen et al., "Lipoprotein metabolism in patients with severe sepsis," *Crit. Care Med. 31*(5): 1359-66 (2003).

Tárnok et al., "Cytometric bead array to measure six cytokines in twenty-five microliters of serum," *Clin. Chem.* 49(6): 1000-02 (2003).

Titus, "Latest assay opens another sepsis frontier," College of American Pathologists, CAP Today, at http://www.cap.org/apps/docs/cap_today/feature_stories/sepsis.html (posted May 2003).

Karzai et al., "Sepsis: definitions and diagnosis," *Int'l J. Crit. Practice 95* (Suppl.): 44-48 (Jun. 1998).

Cariou et al., "The era of genomics: Impact on sepsis clinical trial design," *Crit. Care Med. 30* (Suppl.): S341-48 (2002).

Takala et al., "Markers of inflammation in sepsis," *Annuls Med.* 34: 614-23 (2002).

Anthony et al., "Rapid diagnosis of bacteremia by universal amplification of 23S ribosomal DNA followed by hybridization to an oligonucleotide array," *J. Clin. Microbiol.* 38(2): 781-88 (Feb. 2000).

Petricoin et al., "Use of proteomic patterns in serum to identify ovarian cancer," *Lancet 359*: 572-77 (Feb. 16, 2002).

Ambroise et al., "Selection bias in gene extraction on the basis of microarray gene-expression data," *Proc. Nat'l Acad. Sci. USA* 99(10): 6562-66 (May 14, 2002).

Natanson et al., "The sirens' songs of confirmatory sepsis trials: selection bias and sampling error," *Crit Care Med.* 26(12): 1927-31 (1998).

Llewelyn et al., "Diagnosis of infection in sepsis," *Intensive Care Med.* 27: S10-S32 (2001).

Von Landenberg et al., "New approaches in the diagnosis of sepsis," *Isr. Med. Assoc. J. 3*: 439-42 (Jun. 2001).

Weglöhner et al., "Isolation and characterization of serum procalcitonin from patients with sepsis," *Peptides* 22: 2099-2103(2001).

Beutler et al., "From phenomenon to phenotype and from phenotype to gene: Forward genetics and the problem of sepsis," *J. Infect. Dis. 187* (Suppl. 2): S321-26 (2003).

Marshall et al., "Measures, markers, and mediators: Toward a staging system for clinical sepsis. A report from the Fifth Toronto Sepsis Roundtable, Toronto, Ontario, Canada, Oct. 25-26, 2000," *Crit. Care Med. 31*(5): 1560-67 (2003).

Chinnaiyan et al., "Molecular signatures of sepsis: Multiorgan gene expression profiles of systemic inflammation," *Am. J. Pathol. 159*(4): 1199-1209 (Oct. 2001).

Joyce et al., "Gene Expression Profile of antithrombotic protein C defines new mechanisms modulating inflammation and apoptosis," *J. Biol. Chem.* 276(14): 11,199-203 (Apr. 6, 2001).

Lam et al., "Time course of early and late changes in plasma DNA in trauma patients," *Clin. Chem.* 49(8): 1286-91(2003).

Zhao et al., "Human endothelial cell response to gram-negative lipopolysaccharide assessed with cDNA microarrays," *Am. J. Physiol Cell Physiol. 281*(5): C1587-95 (Nov. 2001).

Shoemaker et al., "Recent developments in DNA microarrays," *Curr. Opinion Microbiol. 5*: 334-37 (2002).

Groeneveld et al., "Circulating inflammatory mediators in patients with fever: predicting bloodstream infection," *Clin. Diag. Lab. Immunol. 8*(6): 1189-95 (Nov. 2001).

Creighton et al., "Expression of matrix metalloproteinase 9 (MMP-9/gelatinase B) in adenocarcinomas strongly correlated with expression of immune response genes," *In Silico Biol. 3*(3): 301-11 (Apr. 7, 2003).

Slotman et al., "Prospectively validated predictions of shock and organ failure in individual septic surgical patients: the Systemic Mediator Associated Response Test," *Crit Care 2000 4*(5):319-26 (Sep. 8, 2000).

Takala et al., "Systemic inflammatory response syndrome without systemic inflammation in acutely ill patients admitted to hospital in a medical emergency," *Clin. Sci. 96*:287-95 (1999).

Angus et al., "Epidemiology of severe sepsis in the United States: analysis of incidence, outcome, and associated costs of care," *Crit. Care Med. 29*(7): 1303-10(2001).

Members of the American College of Chest Physicians/Society of Critical Care Medicine Consensus Conference Committee, "American College of Chest Physicians/Society of Critical Care Medicine Consensus Conference; definitions for sepsis and organ failure and guidelines for the use of innovative therapies in sepsis," *Crit. Care Med. 20*(6): 864-74 (Jun. 1992).

Roumen et al., "Scoring systems and blood lactate concentrations in relation to the development of Adult Respiratory Distress Syndrome and Multiple Organ Failure in severely traumatized patients," *J. Trauma 35*(3): 349-55 (Sep. 1993).

Muret et al., "*Ex vivo* T-lymphocyte derived cytokine production in SIRS patients is influenced by experimental procedures", *Shock 13*(3): 169-74 (2000).

Nadel, "Helping to understand studies examining genetic susceptibility to sepsis," *Clin. Exp. immunol. 127*: 191-92 (2002).

Paterson et al., "Sepsis and the systemic inflammatory response syndrome," *J.R. Coll. Surg. Edinb. 45*: 178-82 (Jun. 2000).

Reinhart et al., "Markers of endothelial damage in organ dysfunction and sepsis," *Crit. Care Med. 30*(5): S302-12.

Healy, "New and emerging therapies for sepsis," *Annuls Pharmacother. 36*: 648-54 (Apr. 2002).

Rangel-Frausto et al., "The natural history of the systemic inflammatory response syndrome (SIRS)," *J. Am. Med. Ass'n 273*: 117-23 (1995).

Weinstein et al., "The clinical significance of positive blood cultures in the 1990s: a prospective comprehensive evaluation of the microbiology, epidemiology, and outcome of bacteremia and fungemia in adults," *Clin. Infectious Diseases 24*: 584-602(1997).

Hastie et al., The Elements of Statistical Learning (Springer-Verlag 2001).

Zou, et. al., "Application of cDNA microarrays to generate a molecular taxonomy capable of distinguishing between colon cancer and normal colon," *Oncogene 21*: 4855-62 (2002).

Hagberg, "From magnetic resonance spectroscopy to classification of tumors: a review of pattern recognition methods," *NMR Biomed. 11*: 148-56(1998).

Stordeur et al., "Cytokine mRNA quantification by real-time PCR," *J. Immunol. Methods 259*: 55-64 (2002).

Tan et al., "The gene expression fingerprint of human heart failure," *Proc. Nat'l Acad. Sci. USA 99*: 11387-92 (2002).

Wei et al., "Desorption-ionization mass spectrometry on porous silicon," *Nature 399*: 243-46(1999).

Sambrook et al., Molecular Cloning ($3^{rd}$ ed., Cold Spring Harbor Laboratory Press 2001).

Harper, Pyrolysis and GC in Polymer Analysis (Marcel Dekker, Inc. 1985).

Wagner et al., "Interpretation of static time-of-flight secondary ion mass spectra of adsorbed protein films by multivariate pattern recognition," *Anal. Chem. 74*: 1824-35 (2002).

Bright et al., "Rapid typing of bacteria using matrix-assisted laser desorption ionization time-of-flight mass spectrometry and pattern recognition software," *J. Microbiol. Methods 48*: 127-38 (2002).

Dalluge, "Mass spectrometry for direct determination of proteins in cells: applications in biotechnology and microbiology," *Fresenius J. Anal. Chem. 366*: 701-11(2000).

Oberholzer et al., "Sepsis syndromes: understanding the role of innate and acquired immunity," *Shock 16*: 83-96 (2001).

Vincent et al., The Sepsis Text (Carlet et al., eds., Kluwer Academic Publishers 2002).

Gagnon et al., "Endoplasmic reticulum-mediated phagocytosis is a mechanism of entry into macrophages," *Cell 110*: 119-31 (2002).

Venables et al., Modern Applied Statistics With S ($4^{th}$ ed., Springer 2002).

Rixen et al., "Sepsis/SIRS', Physiologic Classification, Severity Stratification, Relation to Cytokine Elaboration and Outcome Prediction in Posttrauma Illness," *J. Trauma 41* (4): 581-598(1996).

Selberg et al., "Discrimination of Sepsis and Systematic Inflammatory Response Syndrome by Determination of Circulating Plasma Concentrations of Procalcitonin, Protein Complement 3a, and interleukin-6," *Crit. Care Med. 28* (8): 2793-2798(2000).

Wakefield et al., "Polymorphonuclear Leukocyte Activation. An Early Marker of the Postsurgical Sepsis Response," *Arch. Surg. 128*: 390-395(1993).

Knaus et al., "The Apache III Prognostic System—Risk Prediction of Hospital Morality for Critically Ill Hospitalized Adults," *Chest 100* (6): 1619-1636(1991).

Bone et al., "Definitions for Sepsis and Organ Failure," *Critical Care Medicine 20* (6): 724-726(1992).

Cheadle, "The Human Leukocyte Antigens and Their Relationship to Infection," *The American Journal of Surgery 165* (2A Suppl): 75S-81S(1993).

Wakefield et al., "Changes in Major Histocompatibility Complex Class II Expression in Monocytes and T cells of Patients Developing Infection after Surgery," *British Journal of Surgery 80* (2): 205-209(1993).

Sauata et al., "Early Predictors of Postinjury Multiple Organ Failure," *Arch. Surgery 129*: 39-45(1994).

Wagner et al., "Daily Prognostic Estimates for Critically Ill Adults in Intensive Care Units: Results from a Prospective, Multicenter, Inception Cohort Analysis," *Critical Care Medicine 22* (9): 1359-1372(1994).

Asadullah et al., "Immunodepression Following Neurosurgical Procedures," *Critical Care Medicine 23* (12): 1976-1983(1995).

Wakefield et al., "Surgery and the Release of a Neutrophil Fcy Receptor," *The American Journal of Surgery 170*: 277-284(1995).

Slotman et al., "Multivariate Regression Modeling for the Prediction of Inflammation, Systemic Pressure, and End-organ Function in Severe Sepsis," *Shock 8* (3): 225-231(1997).

Van Den Berk et al., "Low HLA-DR Expression on Monocytes as a Prognostic Marker for Bacterial Sepsis after Liver Transplantation," *Transplantation 63* (12): 1846-1848(1997).

Giannoudis et al., "Stimulation of Inflammatory Markers after Blunt Trauma," *British Journal of Surgery 85*: 986-990(1998).

Millili et al., "Predicting Surgical Outcome Using Bayesian Analysis," *Journal of Surgical Research 77*: 45-49(1998).

Rangel-Frautso et al., "The Dynamics of Disease Progression in Sepsis: Markov Modeling Describing the Natural History and the Likely Impast of Effective Antisepsis Agents," *Clinical Infectious Diseases 27*: 185-190(1998).

Weirich et al., "Neutrophil CD11b Expression as a Diagnostic Marker for Early-Onset Neonatal infection," *The Journal of Pediatrics 132* (ss.3,1): 445-451(1998).

DeBont et al., "Plasma IL-8 and IL-6 Levels can be used to Define a Group of Low Risk of Septicaemia Among Cancer Patients with Fever and Neurtopenia," *British Journal of Haematology 107*: 375-380(1999).

Ditschkowski et al., "HLA-DR Expression and Soluble HLA-DR Levels in Septic Patients after Trauma," *Annals of Surgery 229* (2): 246-254(1999).

Taniguchi et al., "Change in the Ratio of Interleukin-6 to Interleukin-10 Predicts a Poor Outcome in Patients with Systemic Inflammatory Response Syndrome," *Critical Care Medicine* 27 (7): 1262-1264(1999).

Manjuck et al., "Decreased Response to Recall Antigens is Associated with Depressed Costimulatory Receptor Expression in Septic Critically Ill Patients." *Journal Laboratory Clinical Medicine* 135(2): 153-160(2000).

Muller et al., "Calcitonin Precursors are Reliable Markers of Sepsis in a Medical Intensive Care Unit," *Critical Care Medicine* 4: 977-983(2000).

Nupponen et al., "Neutrophil CD11b Expression and Circulating Interleukin-8 as Diagnostic Markers for Early-Onset Neonatal Sepsis," *Pediatrics* 108 (1): 1-6(2001).

Slotman et al., "Prospectively Validated Prediction of Physiologic Variables and Organ Failure in Septic Patents: The Systemic Mediator Associated Response Test (SMART)," *Critical Care Medicine* 30 (5): 1035-1045 (2002).

Oczenski, "HLA-DR as a Marker for Increased Risk for Systemic Inflammation and Septic Complications after Cardiac Surgery," *Intensive Care Medicine* 29: 1253-1257(2003).

Perry et al., "Is Low Monocyte HLA-DR Expression Helpful to Predict Outcome in Severe Sepsis?" *Intensive Care Medicine* 29: 1245-1252(2003).

Kuster et al., 1998, "Interleukin-1 receptor antagonist and interleukin-6 for early diagnosis of neonatal sepsis 2 days before clinical manifestation," Lancet 352(9136):1271-1277.

Smith et al., 2004, "Impact of immunomodulatory oligodeoxynucleotides on cytokine production in the lipopolysaccharide-stimulated human whole blood model," Surgery 136(2):464-472.

Wang et al., 1998, "Tissue coexpression of LBP and CD14 mRNA in a mouse model of sepsis," J. Surg. Res. 76(1):67-73.

Wert et al., 2000, "Increased metalloproteinase activity, oxidant production, and emphysema in surfactant protein D gene-inactivated mice," Proc. Natl. Acad. Sci. USA 97(11):5972-5977.

Zhu et al., 1997, "Effects of prolactin and metoclopramide on macrophage cytokine gene expression in late sepsis," Cytokine 9(6):437-446.

Belobordova et al., 2000, "Small molecules originating from microbes (SMOM) and their role in microbes-host relationship," Microb. Ecol. Health and Disease; 12:12-21.

Brunkhorst et al., 2002, "Diagnostic approach to sepsis-state of the art!," Zentralblatt fur Chirurgie; 127(3):165-173.

Chinnaiyan et al., 2001, "Molecular signatures of sepsis: multiorgan gene expression profiles of systemic inflammation," Am J Pathol. 159(4):1199-209.

Dollner et al., 2001, "Early diagnostic markers for neonatal sepsis: Comparing C-reactive protein, interleukin -6, soluble tumour necrosis factor receptors and soluble adhesion molecules," J Clin Epidemiol; 54(12):1251-7.

Drobnik et al., 2003, "Plasma ceramide and lysophosphatidylcholine inversely correlate with mortality in sepsis patients," J Lipid Res; 44(4):754-61.

Feezor et al., 2003, "Molecular Characterization of the Acute Inflammatory Response to Infections with Gram-Negative versus Gram-Positive Bacteria," Infect Immun; 71(10):5803-13.

Fung et al., 2002, "ProteinChip® Clinical Proteomics: Computational Challenges and Solutions," Biotechniques; Suppl:34-8, 40-1.

Gaut et al., 2001, "Neutrophils employ the myeloperoxidase system to generate antimicrobial brominating and chlorinating oxidants during sepsis," Proc Natl Acad Sci U S A; 98(21):11961-6.

Harbarth et al., 2001, "Diagnostic value of procalcitonin, interleukin-6, and interleukin-8 in critically ill patients admitted with suspected sepsis," Am J Respir Crit Care Med; 164(3):396-402.

Pathan et al., 2003, "The complexity of the inflammatory response to the meningococcal sepsis revealed by gene expression profiling using cDNA microarrays," Crit. Care Med; 31(12 Suppl.): A47.

Presto Elgstoen et al., 2001, "Potential of capillary electrophoresis, tandem mass spectrometry and coupled capillary electrophoresis-tandem mass spectrometry as diagnostic tools," J. Chromatogr. A; 914: 265-275.

Suzuki et al., 2000, "Comprehensive gene expression profile of LPS-stimulated human monocytes by SAGE," Blood; 96(7):2584-91.

Weigand et al., 1999, "Gene Expression Pattern in Human Monocytes as a Surrogate Marker for Systemic Inflammatory Response Syndrome (SIRS)," Mol Med; 5(3):192-202.

Zhang et al., 2001, "Recursvie partitioning for tumor classification with gene expression microarray data," Proc Natl Acad Sci U S A; 98(12):6730-5.

Calandra, J. Chemotherapy, 13:173-180 (2001).

Holmes, Chest, 124:1103-1115 (2003).

Lakhani, Curr. Opin. Pediatr., 15:278-282 (Jun. 2003).

Pugin, American Journal of Respiratory Cell and Molecular Biology, 20(3):458-464 (Mar. 1999).

Read, Curr. Opin. Crit. Care, 7:371-375 (2001).

Yao, Chin. Crit. Care Med., 15:646- (Nov. 2003).

Yassen, Anaesthesia, 56(8):739-732 (Aug. 2001).

Zweigner, Blood, 98:3800-3808(2001).

Affymetrix Details for HG-U95A:32722_AT, pp. 1-4.

Affymetrix Details for HG-U95A:331859_AT, pp. 1-5.

Affymetrix Details for HG-U95A:36377_AT, pp. 1-3.

Affymetrix Product Catalog, Jan. 2001.

Ahern, "Biochemical, Reagents Kits Offer Scientists Good Return on Investment," The Scientist 9(15):20-22 (1995).

Allen et al., "Neutrophil CD64 Expression: Distinguishing Acute Inflammatory Autoimmune Disease from Systemic Infections," Ann. Rheum. Dis., 61:522-525 (2002).

Barth et al., "Peaks of Endogenous G-CSF Serum Concentrations are Followed by an Increase in Respiratory Burst Activity of Granulocytes in Patients with Septic Shock," Cytokine, 17:275-284 (Mar. 2002).

Carraway et al., "Differential Expression of Arginase and iNOS in the Lung in Sepsis," Exp. Lung Res., 24:253-268 (1998).

Ernst et al., "Three Genes for the Human High Affinity Fc Receptor for IgG (FcγRI) Encode Four Distinct Transcription Products," J. of Biol. Chem., 267(22):15692-15700 (1992).

Fischer et al., "CD64 Surface Expression on Neutrophils is Transiently Upregulated in Patients with Septic Shock," Intensive Care Med., 27:1848-1852 (2001).

Genbank GI:13543892, "*Homo sapiens Matrix* Metallopeptidase 9 (gelatinase B, 92kDa Gelatinase, 92kDa Type IV Collagenase), mRNA (cDNA Clone MGC:12688 IMAGE:4054882)," Complete CDS pp. 1-5.

Genbank NM_000566 [GI:24431940], Oct. 31, 2002, *Homo sapiens* Fc fragment of IgG, high affinity la, receptor (CD64) (FCGRIA), mRNA, pp. 1-4, downloaded from http://www.ncbi.nlm.nih.gov/entrez/viewer.fcgi?db=nuccore&id=24431940.

Genbank NM_001172 [GI:10947110], Oct. 23, 2000, *Homo sapiens* arginase, type II (ARG2), nuclear gene encoding mitochondrial protein, mRNA, pp. 1-3, downloaded from http://www.ncbi.nlm.nih.gov/entrez/viewer.fcgi?val=10947110.

Hecker et al., "Inhibition of Arginase by $N^G$-hydroxy-L-arginine in Alveolar Macrophages: Implications for the Utilization of L-Arginine for Nitric Oxide Synthesis," FEBS Letters, 359:251-254 (1995).

Hey et al., "Nitric Oxide Synthase Activity is Inducible in Rat, but not Rabbit Alveolar Macrophages, with a Concomitant Reduction in Arginase Activity," Arch. Pharmacol., 351:651-659 (1995).

Layseca-Espinosa et al., "Expression of CD64 as a Potential Marker of Neonatal Sepsis," Pediatric Allergy and Immunology, 13:319-327 (2002).

Spittler et al., "Relationship Between Interleukin-6 plasma Concentration in Patients with Sepsis, Monocyte Phenotype, Monocyte Phagocytic Properties, and Cytokine Production," Clin. Infectious Diseases, 31:1338-1342 (2000).

Vockley et al., "Cloning and Characterization of Human Type II Arginase Gene," Genomics, 38(2):118-123 (1996).

Wang et al., "Co-Induction of Arginase and Nitric Oxide Synthase in Murine Macrophages Activated by Lipopolysaccharide," Biochem. Biophys. Res. Comm. 210(3):1009-1016 (May 25, 1995).

Weiss et al., "Filgrastim (RHG-CSF) Related Modulation of the Inflammatory Response in Patients at Risk of Sepsis or with Sepsis," Cytokine, 8:260-265 (1996).

Hirayama et al., "Concentrations of Thrombopoietin in Bone Marrow in Normal Subjects and in Patients With Idiopathic Thrombocytopenic Purpura, Aplastic Anemia, and Essential Thrombocythemia Correlate With Its mRNA Expression of Bone Marrow Stromal Cells." Blood, 92:46-52, (Jul. 1, 1998).

Kobold et al., "Leukocyte activation in sepsis; correlations with disease state and mortality," Intensive Care Med, 26:883-892 (2000).

Cobb et al., "Sepsis gene expression profiling: Murine splenic compared with hepatic responses determined by using complementary DNA microarrays," Crit Care Med 30:2711-2721 (2002).

* cited by examiner

SIRS -negative → SIRS -positive

↓

Sepsis

Severe Sepsis

↓

Septic Shock

↓

Multiple Organ Dysfunction

FIGURE 1

DIAGNOSIS OF SEPSIS OR SIRS USING BIOMARKER PROFILES

The present application claims priority to U.S. Provisional Patent Application Ser. No. 60/425,322, filed Nov. 12, 2002, which is herein incorporated by reference in its entirety.

FIELD OF THE INVENTION

The present invention relates to methods of diagnosing or predicting sepsis or its stages of progression in an individual. The present invention also relates to methods of diagnosing systemic inflammatory response syndrome in an individual.

BACKGROUND OF THE INVENTION

Early detection of a disease condition typically allows for a more effective therapeutic treatment with a correspondingly more favorable clinical outcome. In many cases, however, early detection of disease symptoms is problematic; hence, a disease may become relatively advanced before diagnosis is possible. Systemic inflammatory conditions represent one such class of diseases. These conditions, particularly sepsis, typically result from an interaction between a pathogenic microorganism and the host's defense system that triggers an excessive and dysregulated inflammatory response in the host. The complexity of the host's response during the systemic inflammatory response has complicated efforts towards understanding disease pathogenesis. (Reviewed in Healy, Annul. Pharmacother. 36: 648-54 (2002).) An incomplete understanding of the disease pathogenesis, in turn, contributes to the difficulty in finding diagnostic biomarkers. Early and reliable diagnosis is imperative, however, because of the remarkably rapid progression of sepsis into a life-threatening condition.

Sepsis follows a well-described time course, progressing from systemic inflammatory response syndrome ("SIRS") -negative to SIRS-positive to sepsis, which may then progress to severe sepsis, septic shock, multiple organ dysfunction ("MOD"), and ultimately death. Sepsis also may arise in an infected individual when the individual subsequently develops SIRS. "SIRS" is commonly defined as the presence of two or more of the following parameters: body temperature greater than 38° C. or less than 36° C.; heart rate greater than 90 beats per minute; respiratory rate greater than 20 breaths per minute; $P_{CO_2}$ less than 32 mm Hg; and a white blood cell count either less than $4.0 \times 10^9$ cells/L or greater than $12.0 \times 10^9$ cells/L, or having greater than 10% immature band forms. "Sepsis" is commonly defined as SIRS with a confirmed infectious process. "Severe sepsis" is associated with MOD, hypotension, disseminated intravascular coagulation ("DIC") or hypoperfusion abnormalities, including lactic acidosis, oliguria, and changes in mental status. "Septic shock" is commonly defined as sepsis-induced hypotension that is resistant to fluid resuscitation with the additional presence of hypoperfusion abnormalities.

Documenting the presence of the pathogenic microorganisms clinically significant to sepsis has proven difficult. Causative microorganisms typically are detected by culturing a patient's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of patients presenting clinical manifestations of sepsis. (Rangel-Frausto et al., JAMA 273: 117-23 (1995).) Diagnosis can be further complicated by contamination of samples by non-pathogenic microorganisms. For example, only 12.4% of detected microorganisms were clinically significant in a study of 707 patients with septicemia. (Weinstein et al., Clinical Infectious Diseases 24: 584-602 (1997).)

The difficulty in early diagnosis of sepsis is reflected by the high morbidity and mortality associated with the disease. Sepsis currently is the tenth leading cause of death in the United States and is especially prevalent among hospitalized patients in non-coronary intensive care units (ICUs), where it is the most common cause of death. The overall rate of mortality is as high as 35%, with an estimated 750,000 cases per year occurring in the United States alone. The annual cost to treat sepsis in the United States alone is in the order of billions of dollars.

A need, therefore, exists for a method of diagnosing sepsis sufficiently early to allow effective intervention and prevention. Most existing sepsis scoring systems or predictive models predict only the risk of late-stage complications, including death, in patients who already are considered septic. Such systems and models, however, do not predict the development of sepsis itself. What is particularly needed is a way to categorize those patients with SIRS who will or will not develop sepsis. Currently, researchers will typically define a single biomarker that is expressed at a different level in a group of septic patients versus a normal (i.e., non-septic) control group of patients. U.S. patent application Ser. No. 10/400,275, filed Mar. 26, 2003, the entire contents of which are hereby incorporated by reference, discloses a method of indicating early sepsis by analyzing time-dependent changes in the expression level of various biomarkers. Accordingly, optimal methods of diagnosing early sepsis currently require both measuring a plurality of biomarkers and monitoring the expression of these biomarkers over a period of time.

There is a continuing urgent need in the art to diagnose sepsis with specificity and sensitivity, without the need for monitoring a patient over time. Ideally, diagnosis would be made by a technique that accurately, rapidly, and simultaneously measures a plurality of biomarkers at a single point in time, thereby minimizing disease progression during the time required for diagnosis.

SUMMARY OF THE INVENTION

The present invention allows for accurate, rapid, and sensitive prediction and diagnosis of sepsis through a measurement of more than one biomarker taken from a biological sample at a single point in time. This is accomplished by obtaining a biomarker profile at a single point in time from an individual, particularly an individual at risk of developing sepsis, having sepsis, or suspected of having sepsis, and comparing the biomarker profile from the individual to a reference biomarker profile. The reference biomarker profile may be obtained from a population of individuals (a "reference population") who are, for example, afflicted with sepsis or who are suffering from the onset of sepsis or a particular stage in the progression of sepsis. If the biomarker profile from the individual contains appropriately characteristic features of the biomarker profile from the reference population, then the individual is diagnosed as having a more likely chance of becoming septic, as being afflicted with sepsis or as being at the particular stage in the progression of sepsis as the reference population. The reference biomarker profile may also be obtained from various populations of individuals including those who are suffering from SIRS or those who are suffering from an infection but who are not suffering from SIRS. Accordingly, the present invention allows the clinician to determine, inter alia, those patients who do not have SIRS, who have SIRS but are not likely to develop sepsis within the time frame of the investigation, who have sepsis, or who are at risk of eventually becoming septic.

Although the methods of the present invention are particularly useful for detecting or predicting the onset of sepsis in SIRS patients, one of ordinary skill in the art will understand that the present methods may be used for any patient including, but not limited to, patients suspected of having SIRS or of being at any stage of sepsis. For example, a biological sample could be taken from a patient, and a profile of biomarkers in the sample could be compared to several different reference biomarker profiles, each profile derived from individuals such as, for example, those having SIRS or being at a particular stage of sepsis. Classification of the patient's biomarker profile as corresponding to the profile derived from a particular reference population is predictive that the patient falls within the reference population. Based on the diagnosis resulting from the methods of the present invention, an appropriate treatment regimen could then be initiated.

Existing methods for the diagnosis or prediction of SIRS, sepsis or a stage in the progression of sepsis are based on clinical signs and symptoms that are nonspecific; therefore, the resulting diagnosis often has limited clinical utility. Because the methods of the present invention accurately detect various stages of sepsis, they can be used to identify those individuals who might appropriately be enrolled in a therapeutic study. Because sepsis may be predicted or diagnosed from a "snapshot" of biomarker expression in a biological sample obtained at a single point in time, this therapeutic study may be initiated before the onset of serious clinical symptoms. Because the biological sample is assayed for its biomarker profile, identification of the particular biomarkers is unnecessary. Nevertheless, the present invention provides methods to identify specific biomarkers of the profiles that are characteristic of sepsis or of a particular stage in the progression of sepsis. Such biomarkers themselves will be useful tools in predicting or diagnosing sepsis.

Accordingly, the present invention provides, inter alia, methods of predicting the onset of sepsis in an individual. The methods comprise obtaining a biomarker profile at a single point in time from the individual and comparing the individual's biomarker profile to a reference biomarker profile. Comparison of the biomarker profiles can predict the onset of sepsis in the individual with an accuracy of at least about 60%. The individual's biomarker profile and the reference biomarker profile comprise features that are measurable characteristics of a nucleic acid. This method may be repeated again at any time prior to the onset of sepsis.

The present invention also provides, inter alia, a method of diagnosing sepsis in an individual having or suspected of having sepsis comprising obtaining a biomarker profile at a single point in time from the individual and comparing the individual's biomarker profile to a reference biomarker profile. The individual's biomarker profile and the reference biomarker profile comprise features that are measurable characteristics of a nucleic acid. Comparison of the biomarker profiles can diagnose sepsis in the individual with an accuracy of at least about 60%. This method may be repeated on the individual at any time.

The present invention further provides, inter alia, methods of determining the progression (i.e., the stage) of sepsis in an individual having or suspected of having sepsis. This method comprises obtaining a biomarker profile at a single point in time from the individual and comparing the individual's biomarker profile to a reference biomarker profile. The individual's biomarker profile and the reference biomarker profile comprise features that are measurable characteristics of a nucleic acid. Comparison of the biomarker profiles can determine the progression of sepsis in the individual with an accuracy of at least about 60%. This method may also be repeated on the individual at any time.

Additionally, the present invention provides, inter alia, a method of diagnosing SIRS in an individual having or suspected of having SIRS. This method comprises obtaining a biomarker profile at a single point in time from the individual and comparing the individual's biomarker profile to a reference biomarker profile. The individual's biomarker profile and the reference biomarker profile comprise features that are measurable characteristics of a nucleic acid. Comparison of the biomarker profiles can diagnose SIRS in the individual with an accuracy of at least about 60%. This method may also be repeated on the individual at any time.

In another embodiment, the invention provides, inter alia, a method of determining the status of sepsis or of diagnosing SIRS in an individual comprising applying a decision rule. The decision rule comprises comparing (i) a nucleic acid biomarker profile generated from a biological sample taken from the individual at a single point in time with (ii) a nucleic acid biomarker profile generated from a reference population. Application of the decision rule determines the status of sepsis or diagnoses SIRS in the individual. The method may be repeated on the individual at one or more separate, single points in time.

The present invention further provides, inter alia, a method of determining the status of sepsis or diagnosing SIRS in an individual comprising obtaining a biomarker profile from a biological sample taken from the individual and comparing the individual's biomarker profile to a reference biomarker profile, where the individual's biomarker profile and the reference biomarker profile comprise features that are measurable characteristics of a nucleic acid. A single such comparison is capable of classifying the individual as belonging to or not belonging to the reference population. Comparison of the biomarker profiles also determines the status of sepsis or diagnoses SIRS in the individual.

The invention further provides, inter alia, a method of determining the status of sepsis or diagnosing SIRS in an individual comprising obtaining a biomarker profile from a biological sample taken from the individual and comparing the individual's biomarker profile to a reference biomarker profile obtained from biological samples from a reference population. The reference population may be selected from the group consisting of a normal reference population, a SIRS-positive reference population, an infected/SIRS-negative reference population, a sepsis-positive reference population, a reference population at a stage in the progression of sepsis, a SIRS-positive reference population confirmed as having sepsis by conventional techniques after about 0-36 hours, a SIRS-positive reference population confirmed as having sepsis by conventional techniques after about 36-60 hours, and a SIRS-positive reference population confirmed as having sepsis by conventional techniques after about 60-84 hours. The individual's biomarker profile and the reference biomarker profile comprise features that are measurable characteristics of a nucleic acid. A single such comparison is capable of classifying the individual as having membership in the reference population, and the comparison determines the status of sepsis or diagnoses SIRS in the individual.

In yet another embodiment, the present invention provides, inter alia, a method of determining the status of sepsis or diagnosing SIRS in an individual where the method comprises comparing a measurable characteristic of at least one nucleic acid biomarker between (i) a biomarker profile obtained from a biological sample from the individual and (ii) a biomarker profile obtained from biological samples from a reference population. Based on this comparison, the individual is classified as belonging to or not belonging to the reference population. The comparison also determines the status of sepsis or diagnoses SIRS in the individual. The nucleic acid biomarkers, in one embodiment, are selected from the group of biomarkers shown in any one of TABLES 2-10.

In a further embodiment, the present invention provides, inter alia, a method of determining the status of sepsis or diagnosing SIRS in an individual comprising selecting at least two features from a set of nucleic acid biomarkers in a biomarker profile generated from a biological sample of an individual. These features are compared to a set of the same nucleic acid biomarkers in a biomarker profile generated from biological samples from a reference population. A single such comparison is capable of classifying the individual as having membership in the reference population with an accuracy of at least about 60%, and the comparison determines the status of sepsis or diagnoses SIRS in the individual.

The present invention also provides, inter alia, a method of determining the status of sepsis or diagnosing SIRS in an individual comprising determining the changes in the abundance of at least two nucleic acid biomarkers contained in a biological sample of an individual and comparing the changes in the abundance of these biomarkers to the changes in the abundance of these biomarkers in biological samples from a reference population. Alternatively, the abundance of the at least two nucleic acid biomarkers in the individual's biomarker profile may be compared to the abundance of the at least two nucleic acids in the biomarker profile of the reference population. Both comparisons are capable of classifying the individual as having membership in the reference population, and the comparisons determine the status of sepsis or diagnoses SIRS in the individual.

In another embodiment, the invention provides, inter alia, a method of determining the status of sepsis in an individual, comprising determining changes in the abundance or the abundance of at least one, two, three, four, five, 10 or 20 or more nucleic acid biomarkers as compared to changes in the abundance or the abundance of the at least one nucleic acid biomarker for biological samples from a reference population that contracted sepsis and a reference population that did not. The nucleic acid biomarkers are selected from the group consisting of the nucleic acids listed in any one of TABLES 2-10.

BRIEF DESCRIPTION OF THE DRAWINGS

FIG. 1 illustrates the progression of SIRS to sepsis. The condition of sepsis consists of at least three stages, with a septic patient progressing from severe sepsis to septic shock to multiple organ dysfunction.

DETAILED DESCRIPTION OF THE PREFERRED EMBODIMENTS

Figure 2:
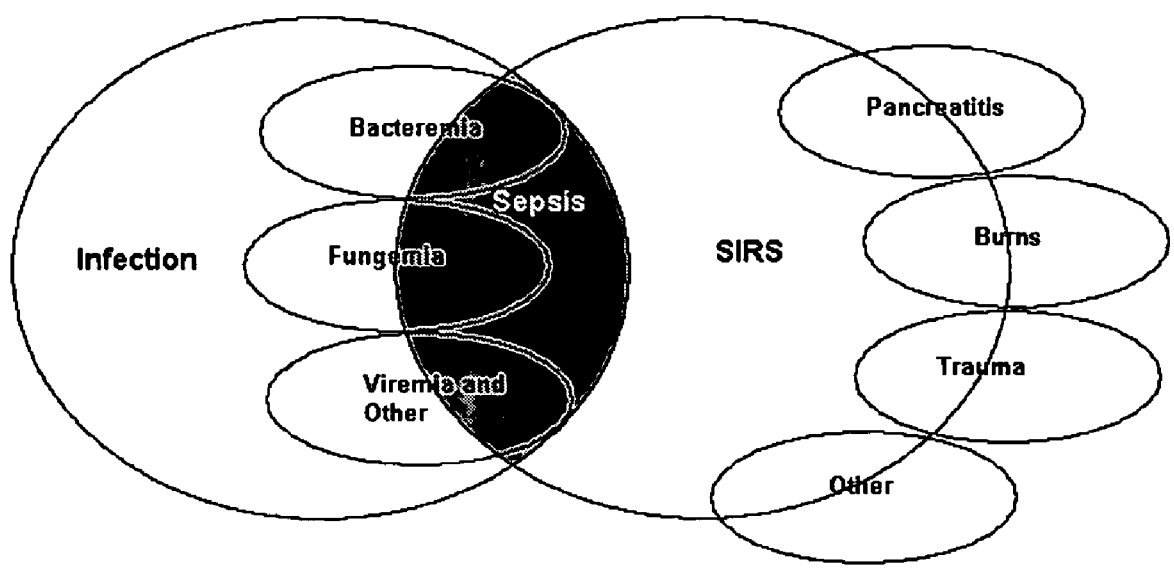
FIG. 2 shows the relationship between sepsis and SIRS. The various sets shown in the Venn diagram correspond to populations of individuals having the indicated condition.

The present invention allows for the rapid, sensitive, and accurate diagnosis or prediction of sepsis using one or more biological samples obtained from an individual at a single time point ("snapshot") or during the course of disease progression. Advantageously, sepsis may be diagnosed or predicted prior to the onset of clinical symptoms, thereby allowing for more effective therapeutic intervention.

"Systemic inflammatory response syndrome," or "SIRS," refers to a clinical response to a variety of severe clinical insults, as manifested by two or more of the following conditions within a 24-hour period:
  body temperature greater than 38° C. (100.4° F.) or less than 36° C. (96.8° F.);
  heart rate (HR) greater than 90 beats/minute;
  respiratory rate (RR) greater than 20 breaths/minute, or $P_{CO2}$ less than 32 mm Hg, or requiring mechanical ventilation; and
  white blood cell count (WBC) either greater than $12.0 \times 10^9$/L or less than $4.0 \times 10^9$/L or having greater than 10% immature forms (bands).

These symptoms of SIRS represent a consensus definition of SIRS that may be modified or supplanted by an improved definition in the future. The present definition is used to clarify current clinical practice and does not represent a critical aspect of the invention.

A patient with SIRS has a clinical presentation that is classified as SIRS, as defined above, but is not clinically deemed to be septic. Individuals who are at risk of developing sepsis include patients in an ICU and those who have otherwise suffered from a physiological trauma, such as a burn or other insult. "Sepsis" refers to a SIRS-positive condition that is associated with a confirmed infectious process. Clinical suspicion of sepsis arises from the suspicion that the SIRS-positive condition of a SIRS patient is a result of an infectious process. As used herein, "sepsis" includes all stages of sepsis including, but not limited to, the onset of sepsis, severe sepsis and MOD associated with the end stages of sepsis.

The "onset of sepsis" refers to an early stage of sepsis, i.e., prior to a stage when the clinical manifestations are sufficient to support a clinical suspicion of sepsis. Because the methods of the present invention are used to detect sepsis prior to a time that sepsis would be suspected using conventional techniques, the patient's disease status at early sepsis can only be confirmed retrospectively, when the manifestation of sepsis is more clinically obvious. The exact mechanism by which a patient becomes septic is not a critical aspect of the invention. The methods of the present invention can detect changes in the biomarker profile independent of the origin of the infectious process. Regardless of how sepsis arises, the methods of the present invention allow for determining the status of a patient having, or suspected of having, sepsis or SIRS, as classified by previously used criteria.

"Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status. "Septic shock" refers to sepsis-induced hypotension that is not responsive to adequate intravenous fluid challenge and with manifestations of peripheral hypoperfusion. A "converter patient" refers to a SIRS-positive patient who progresses to clinical suspicion of sepsis during the period the patient is monitored, typically during an ICU stay. A "non-converter patient" refers to a SIRS-positive patient who does not progress to clinical suspicion of sepsis during the period the patient is monitored, typically during an ICU stay.

A "biomarker" is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the biological sample and that may be isolated from, or measured in, the biological sample. Furthermore, a biomarker can be the entire intact molecule, or it can be a portion thereof that may be partially functional or recognized, for example, by an antibody or other specific binding protein. A biomarker is considered to be informative if a measurable aspect of the biomarker is associated with a given state of the patient, such as a particular stage of sepsis. Such a measurable aspect may include, for example, the presence, absence, or concentration of the biomarker in the biological sample from the individual and/or its presence as part of a profile of biomarkers. Such a measurable aspect of a biomarker is defined herein as a "feature." A feature may also be a ratio of two or more measurable aspects of biomarkers, which biomarkers may or may not be of known identity, for example. A "biomarker profile" comprises at least two such features, where the features can correspond to the same or different classes of biomarkers such as, for example, a nucleic acid and a carbohydrate. A biomarker profile may also comprise at least three, four, five, 10, 20, 30 or more features. In one embodiment, a biomarker profile comprises hundreds, or even thousands, of features. In another embodiment, the biomarker profile comprises at least one measurable aspect of at least one internal standard.

A "phenotypic change" is a detectable change in a parameter associated with a given state of the patient. For instance, a phenotypic change may include an increase or decrease of a biomarker in a bodily fluid, where the change is associated with sepsis or the onset of sepsis. A phenotypic change may further include a change in a detectable aspect of a given state of the patient that is not a change in a measurable aspect of a biomarker. For example, a change in phenotype may include a detectable change in body temperature, respiration rate, pulse, blood pressure, or other physiological parameter. Such changes can be determined via clinical observation and measurement using conventional techniques that are well-known to the skilled artisan. As used herein, "conventional techniques" are those techniques that classify an individual based on phenotypic changes without obtaining a biomarker profile according to the present invention.

A "decision rule" is a method used to classify patients. This rule can take on one or more forms that are known in the art, as exemplified in Hastie et al., in "The Elements of Statistical Learning," Springer-Verlag (Springer, N.Y. (2001)), herein incorporated by reference in its entirety. Analysis of biomarkers in the complex mixture of molecules within the sample generates features in a data set. A decision rule may be used to act on a data set of features to predict the onset of sepsis, to determine the progression of sepsis, to diagnose sepsis, or to diagnose SIRS.

The application of the decision rule does not require perfect classification. A classification may be made with at least about 90% certainty, or even more, in one embodiment. In other embodiments, the certainty is at least about 80%, at least about 70%, or at least about 60%. The useful degree of certainty may vary, depending on the particular method of the present invention. "Certainty" is defined as the total number of accurately classified individuals divided by the total number of individuals subjected to classification. As used herein, "certainty" means "accuracy." Classification may also be characterized by its "sensitivity." The "sensitivity" of classification relates to the percentage of sepsis patients who were correctly identified as having sepsis. "Sensitivity" is defined in the art as the number of true positives divided by the sum of true positives and false negatives. In contrast, the "specificity" of the method is defined as the percentage of patients who were correctly identified as not having sepsis. That is, "specificity" relates to the number of true negatives divided by the sum of true negatives and false positives. In one embodiment, the sensitivity and/or specificity is at least about 90%, at least about 80%, at least about 70% or at least about 60%. The number of features that may be used to classify an individual with adequate certainty is typically about four. Depending on the degree of certainty sought, however, the number of features may be more or less, but in all cases is at least one. In one embodiment, the number of features that may be used to classify an individual is optimized to allow a classification of an individual with high certainty.

"Determining the status" of sepsis or SIRS in a patient encompasses classification of a patient's biomarker profile to (1) detect the presence of sepsis or SIRS in the patient, (2) predict the onset of sepsis or SIRS in the patient, or (3) measure the progression of sepsis in a patient. "Diagnosing" sepsis or SIRS means to identify or detect sepsis or SIRS in the patient. Because of the greater sensitivity of the present invention to detect sepsis before an overtly observable clinical manifestation, the identification or detection of sepsis includes the detection of the onset of sepsis, as defined above. That is, "predicting the onset of sepsis" means to classify the patient's biomarker profile as corresponding to the profile derived from individuals who are progressing from a particular stage of SIRS to sepsis or from a state of being infected to sepsis (i.e., from infection to infection with concomitant SIRS). "Detecting the progression" or "determining the progression" of sepsis or SIRS means to classify the biomarker profile of a patient who is already diagnosed as having sepsis or SIRS. For instance, classifying the biomarker profile of a patient who has been diagnosed as having sepsis can encompass detecting or determining the progression of the patient from sepsis to severe sepsis or to sepsis with MOD.

According to the present invention, sepsis may be diagnosed or predicted by obtaining a profile of biomarkers from a sample obtained from an individual. As used herein, "obtain" means "to come into possession of." The present invention is particularly useful in predicting and diagnosing sepsis in an individual who has an infection, or even sepsis, but who has not yet been diagnosed as having sepsis, who is suspected of having sepsis, or who is at risk of developing sepsis. In the same manner, the present invention may be used to detect and diagnose SIRS in an individual. That is, the present invention may be used to confirm a clinical suspicion of SIRS. The present invention also may be used to detect various stages of the sepsis process such as infection, bacteremia, sepsis, severe sepsis, septic shock and the like.

The profile of biomarkers obtained from an individual, i.e., the test biomarker profile, is compared to a reference biomarker profile. The reference biomarker profile can be generated from one individual or a population of two or more individuals. The population, for example, may comprise three, four, five, ten, 15, 20, 30, 40, 50 or more individuals. Furthermore, the reference biomarker profile and the individual's (test) biomarker profile that are compared in the methods of the present invention may be generated from the same individual, provided that the test and reference biomarker profiles are generated from biological samples taken at different time points and compared to one another. For example, a sample may be obtained from an individual at the start of a study period. A reference biomarker profile taken from that sample may then be compared to biomarker profiles generated from subsequent samples from the same individual. Such a comparison may be used, for example, to determine the status of sepsis in the individual by repeated classifications over time.

The reference populations may be chosen from individuals who do not have SIRS ("SIRS-negative"), from individuals who do not have SIRS but who are suffering from an infectious process, from individuals who are suffering from SIRS without the presence of sepsis ("SIRS-positive"), from individuals who are suffering from the onset of sepsis, from individuals who are sepsis-positive and suffering from one of the stages in the progression of sepsis, or from individuals with a physiological trauma that increases the risk of developing sepsis. Furthermore, the reference populations may be SIRS-positive and are then subsequently diagnosed with sepsis using conventional techniques. For example, a population of SIRS-positive patients used to generate the reference profile may be diagnosed with sepsis about 24, 48, 72, 96 or more hours after biological samples were taken from them for the purposes of generating a reference biomarker profile. In one embodiment, the population of SIRS-positive individuals is diagnosed with sepsis using conventional techniques about 0-36 hours, about 36-60 hours, about 60-84 hours, or about 84-108 hours after the biological samples were taken. If the biomarker profile is indicative of sepsis or one of its stages of progression, a clinician may begin treatment prior to the manifestation of clinical symptoms of sepsis. Treatment typically will involve examining the patient to determine the source of the infection. Once locating the source, the clinician typically will obtain cultures from the site of the infection, preferably before beginning relevant empirical antimicrobial therapy and perhaps additional adjunctive therapeutic measures, such as draining an abscess or removing an infected catheter. Therapies for sepsis are reviewed in Healy, supra.

The methods of the present invention comprise comparing an individual's biomarker profile with a reference biomarker profile. As used herein, "comparison" includes any means to discern at least one difference in the individual's and the reference profiles. Thus, a comparison may include a visual inspection of chromatographic spectra, and a comparison may include arithmetical or statistical comparisons of values assigned to the features of the profiles. Such statistical comparisons include, but are not limited to, applying a decision rule. If the biomarker profiles comprise at least one internal standard, the comparison to discern a difference in the biomarker profiles may also include features of these internal standards, such that features of the biomarker are correlated to features of the internal standards. The comparison can predict the chances of acquiring sepsis or SIRS; or the comparison can confirm the presence or absence of sepsis or SIRS; or the comparison can indicate the stage of sepsis at which an individual may be.

The present invention, therefore, obviates the need to conduct time-intensive assays over a monitoring period, as well as the need to identify each biomarker. Although the invention does not require a monitoring period to classify an individual, it will be understood that repeated classifications of the individual, i.e., repeated snapshots, may be taken over time until the individual is no longer at risk. Alternatively, a profile of biomarkers obtained from the individual may be compared to one or more profiles of biomarkers obtained from the same individual at different points in time. The artisan will appreciate that each comparison made in the process of repeated classifications is capable of classifying the individual as having membership in the reference population.

Individuals having a variety of physiological conditions corresponding to the various stages in the progression of sepsis, from the absence of sepsis to MOD, may be distinguished by a characteristic biomarker profile. As used herein, an "individual" is an animal, preferably a mammal, more preferably a human or non-human primate. The terms "individual," "subject" and "patient" are used interchangeably herein. The individual can be normal, suspected of having SIRS or sepsis, at risk of developing SIRS or sepsis, or confirmed as having SIRS or sepsis. While there are many known biomarkers that have been implicated in the progression of sepsis, not all of these markers appear in the initial, pre-clinical stages. The subset of biomarkers characteristic of early-stage sepsis may, in fact, be determined only by a retrospective analysis of samples obtained from individuals who ultimately manifest clinical symptoms of sepsis. Without being bound by theory, even an initial pathologic infection that results in sepsis may provoke physiological changes that are reflected in particular changes in biomarker expression. Once the characteristic biomarker profile of a stage of sepsis, for example, is determined, the profile of biomarkers from a biological sample obtained from an individual may be compared to this reference profile to determine whether the test subject is also at that particular stage of sepsis.

The progression of a population from one stage of sepsis to another, or from normalcy (i.e., a condition characterized by not having sepsis or SIRS) to sepsis or SIRS and vice versa, will be characterized by changes in biomarker profiles, as certain biomarkers are expressed at increasingly higher levels and the expression of other biomarkers becomes down regulated. These changes in biomarker profiles may reflect the progressive establishment of a physiological response in the reference population to infection and/or inflammation, for example. The skilled artisan will appreciate that the biomarker profile of the reference population also will change as a physiological response subsides. As stated above, one of the advantages of the present is the capability of classifying an individual, using a biomarker profile from a single biological sample, as having membership in a particular population. The artisan will appreciate, however, that the determination of whether a particular physiological response is becoming established or is subsiding may be facilitated by a subsequent classification of the individual. To this end, the present invention provides numerous biomarkers that both increase and decrease in level of expression as a physiological response to sepsis or SIRS is established or subsides. For example, an investigator can select a feature of an individual's biomarker profile that is known to change in intensity as a physiological response to sepsis becomes established. A comparison of the same feature in a profile from a subsequent biological sample from the individual can establish whether the individual is progressing toward more severe sepsis or is progressing toward normalcy.

The molecular identity of biomarkers is not essential to the invention. Indeed, the present invention should not be limited to biomarkers that have previously been identified. (See U.S. patent application Ser. No. 10/400,275, filed Mar. 26, 2003.) It is, therefore, expected that novel biomarkers will be identified that are characteristic of a given population of individuals, especially a population in one of the early stages of sepsis. In one embodiment of the present invention, a biomarker is identified and isolated. It then may be used to raise a specifically-binding antibody, which can facilitate biomarker detection in a variety of diagnostic assays. For this purpose, any immunoassay may use any antibodies, antibody fragment or derivative that is capable of binding the biomarker molecules (e.g., Fab, Fv, or scFv fragments). Such immunoassays are well-known in the art. If the biomarker is a protein, it may be sequenced and its encoding gene may be cloned using well-established techniques.

The methods of the present invention may be employed to screen, for example, patients admitted to an ICU. A biological sample such as, for example, blood, is taken immediately upon admission. The complex mixture of proteins and other molecules within the blood is resolved as a profile of biomarkers. This may be accomplished through the use of any technique or combination of techniques that reproducibly distinguishes these molecules on the basis of some physical or chemical property. In one embodiment, the molecules are immobilized on a matrix and then are separated and distinguished by laser desorption/ionization time-of-flight mass spectrometry. A spectrum is created by the characteristic desorption pattern that reflects the mass/charge ratio of each molecule or its fragments. In another embodiment, biomarkers are selected from the various mRNA species obtained from a cellular extract, and a biomarker profile is obtained by hybridizing the individual's mRNA species to an array of cDNAs. The diagnostic use of cDNA arrays is well-known in the art. (See, e.g., Zou, et. al., *Oncogene* 21: 4855-4862 (2002).) In yet another embodiment, a profile may be obtained using a combination of protein and nucleic acid separation methods.

The invention also provides kits that are useful in determining the status of sepsis or diagnosing SIRS in an individual. The kits of the present invention comprise at least one biomarker. Specific biomarkers useful in the present invention are set forth herein. The biomarkers of the kit can be used to generate biomarker profiles according to the present invention. Generally, the biomarkers of the kit will bind, with at least some specificity, to the biomarker molecules contained in the biological sample from which the biomarker profile is generated. Examples of classes of compounds of the kit include, but are not to, proteins, and fragments thereof, peptides, polypeptides, proteoglycans, glycoproteins, lipoproteins, carbohydrates, lipids, nucleic acids, organic and inorganic chemicals, and natural and synthetic polymers. The biomarker(s) may be part of an array, or the biomarker(s) may be packaged separately and/or individually. The kit may also comprise at least one internal standard to be used in generating the biomarker profiles of the present invention. Likewise, the internal standards can be any of the classes of compounds described above. The kits of the present invention also may contain reagents that can be used to detectably label biomarkers contained in the biological samples from which the biomarker profiles are generated. For this purpose, the kit may comprise a set of antibodies or functional fragments thereof that specifically bind at least two, three, four, five, 10, 20 or more of the biomarkers set forth in any one of the following TABLES that list biomarkers. The antibodies themselves may be detectably labeled. The kit also may comprise a specific biomarker binding component, such as an aptamer. If the biomarkers comprise a nucleic acid, the kit may provide an oligonucleotide probe that is capable of forming a duplex with the biomarker or with a complementary strand of a biomarker. The oligonucleotide probe may be detectably labeled.

The kits of the present invention may also include pharmaceutical excipients, diluents and/or adjuvants when the biomarker is to be used to raise an antibody. Examples of pharmaceutical adjuvants include, but are not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of an injectable pharmaceutical form can be brought about by the inclusion of agents which delay absorption such as aluminum monostearate and gelatin.

Generation of Biomarker Profiles

According to one embodiment, the methods of the present invention comprise obtaining a profile of biomarkers from a biological sample taken from an individual. The biological sample may be blood, plasma, saliva, serum, sputum, urine, cerebral spinal fluid, cells, a cellular extract, a tissue sample, a tissue biopsy, a stool sample and the like. The reference biomarker profile may be obtained, for example, from a population of individuals selected from the group consisting of SIRS-negative individuals, SIRS-positive individuals, individuals who are suffering from the onset of sepsis and individuals who already have sepsis. The reference biomarker profile from individuals who already have sepsis may be obtained at any stage in the progression of sepsis, such as infection, bacteremia, severe sepsis, septic shock or MOD.

In one embodiment, a separation method may be used to create a profile of biomarkers, such that only a subset of biomarkers within the sample is analyzed. For example, the biomarkers that are analyzed in a sample may consist of mRNA species from a cellular extract, which has been fractionated to obtain only the nucleic acid biomarkers within the sample, or the biomarkers may consist of a fraction of the total complement of proteins within the sample, which have been fractionated by chromatographic techniques. Alternatively, a profile of biomarkers may be created without employing a separation method. For example, a biological sample may be interrogated with a labeled compound that forms a specific complex with a biomarker in the sample, where the intensity of the label in the specific complex is a measurable characteristic of the biomarker. A suitable compound for forming such a specific complex is a labeled antibody. In one embodiment, a biomarker is measured using an antibody with an amplifiable nucleic acid as a label. In yet another embodiment, the nucleic acid label becomes amplifiable when two antibodies, each conjugated to one strand of a nucleic acid label, interact with the biomarker, such that the two nucleic acid strands form an amplifiable nucleic acid.

In another embodiment, the biomarker profile may be derived from an assay, such as an array, of nucleic acids, where the biomarkers are the nucleic acids or complements thereof. For example, the biomarkers may be ribonucleic acids. The biomarker profile also may be obtained using a method selected from the group consisting of nuclear magnetic resonance, nucleic acid arrays, dot blotting, slot blotting, reverse transcription amplification and Northern analysis. In another embodiment, the biomarker profile is detected immunologically by reacting antibodies, or functional fragments thereof, specific to the biomarkers. A functional fragment of an antibody is a portion of an antibody that retains at least some ability to bind to the antigen to which the complete antibody binds. The fragments, which include, but are not limited to, scFv fragments, Fab fragments and F(ab)$_2$ fragments, can be recombinantly produced or enzymatically produced. In another embodiment, specific binding molecules other than antibodies, such as aptamers, may be used to bind the biomarkers. In yet another embodiment, the biomarker profile may comprise a measurable aspect of an infectious agent or a component thereof. In yet another embodiment, the biomarker profile may comprise measurable aspects of small molecules, which may include fragments of proteins or nucleic acids, or which may include metabolites.

Biomarker profiles may be generated by the use of one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Other suitable separation methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

Biomarker profiles also may be generated by methods that do not require physical separation of the biomarkers themselves. For example, nuclear magnetic resonance (NMR) spectroscopy may be used to resolve a profile of biomarkers from a complex mixture of molecules. An analogous use of NMR to classify tumors is disclosed in Hagberg, *NMR Biomed.* 11: 148-56 (1998), for example. Additional procedures include nucleic acid amplification technologies, which may be used to generate a profile of biomarkers without physical separation of individual biomarkers. (See Stordeur et al., *J. Immunol. Methods* 259: 55-64 (2002) and Tan et al., *Proc. Nat'l Acad. Sci. USA* 99: 11387-11392 (2002), for example.)

In one embodiment, laser desorption/ionization time-of-flight mass spectrometry is used to create a profile of biomarkers where the biomarkers are proteins or protein fragments that have been ionized and vaporized off an immobilizing support by incident laser radiation. A profile is then created by the characteristic time-of-flight for each protein, which depends on its mass-to-charge ("m/z") ratio. A variety of laser desorption/ionization techniques are known in the art. (See, e.g., Guttman et al., *Anal. Chem.* 73: 1252-62 (2001) and Wei et al., *Nature* 399: 243-46 (1999).)

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 µL, with or without prior purification or fractionation. The lysates or sample can be concentrated or diluted prior to application onto the support surface. Laser desorption/ionization is then used to generate mass spectra of the sample, or samples, in as little as three hours.

In another embodiment, the total mRNA from a cellular extract of the individual is assayed, and the various mRNA species that are obtained from the biological sample are used as biomarkers. Profiles may be obtained, for example, by hybridizing these mRNAs to an array of probes, which may comprise oligonucleotides or cDNAs, using standard methods known in the art. Alternatively, the mRNAs may be subjected to gel electrophoresis or blotting methods such as dot blots, slot blots or Northern analysis, all of which are known in the art. (See, e.g., Sambrook et al. in "Molecular Cloning, $3^{rd}$ ed.," Cold Spring Harbor Laboratory Press, Cold Spring Harbor, N.Y. (2001).) mRNA profiles also may be obtained by reverse transcription followed by amplification and detection of the resulting cDNAs, as disclosed by Stordeur et al., supra, for example. In another embodiment, the profile may be obtained by using a combination of methods, such as a nucleic acid array combined with mass spectroscopy.

Use of a Data Analysis Algorithm

In one embodiment, comparison of the individual's biomarker profile to a reference biomarker profile comprises applying a decision rule. The decision rule can comprise a data analysis algorithm, such as a computer pattern recognition algorithm. Other suitable algorithms include, but are not limited to, logistic regression or a nonparametric algorithm that detects differences in the distribution of feature values (e.g., a Wilcoxon Signed Rank Test). The decision rule may be based upon one, two, three, four, five, 10, 20 or more features. In one embodiment, the decision rule is based on hundreds or more of features. Applying the decision rule may also comprise using a classification tree algorithm. For example, the reference biomarker profile may comprise at least three features, where the features are predictors in a classification tree algorithm. The data analysis algorithm predicts membership within a population (or class) with an accuracy of at least about 60%, at least about 70%, at least about 80% and at least about 90%.

Suitable algorithms are known in the art, some of which are reviewed in Hastie et al., supra. Such algorithms classify complex spectra from biological materials, such as a blood sample, to distinguish individuals as normal or as possessing biomarker expression levels characteristic of a particular disease state. While such algorithms may be used to increase the speed and efficiency of the application of the decision rule and to avoid investigator bias, one of ordinary skill in the art will realize that computer-based algorithms are not required to carry out the methods of the present invention.

Algorithms may be applied to the comparison of biomarker profiles, regardless of the method that was used to generate the biomarker profile. For example, suitable algorithms can be applied to biomarker profiles generated using gas chromatography, as discussed in Harper, "Pyrolysis and GC in Polymer Analysis" Dekker, New York (1985). Further, Wagner et al., *Anal. Chem* 74: 1824-35 (2002) disclose an algorithm that improves the ability to classify individuals based on spectra obtained by static time-of-flight secondary ion mass spectrometry (TOF-SIMS). Additionally, Bright et al., *J. Microbiol. Methods* 48: 127-38 (2002) disclose a method of distinguishing between bacterial strains with high certainty (79-89% correct classification rates) by analysis of MALDI-TOF-MS spectra. Dalluge, *Fresenius J. Anal. Chem.* 366: 701-11 (2000) discusses the use of MALDI-TOF-MS and liquid chromatography-electrospray ionization mass spectrometry (LC/ESI-MS) to classify profiles of biomarkers in complex biological samples.

Biomarkers

The methods of the present invention can be carried out by generation of a biomarker profile that is diagnostic or predictive of sepsis or SIRS. Because profile generation is sufficient to carry out the invention, the biomarkers that constitute the profile need not be known or subsequently identified.

Biomarkers that can be used to generate the biomarker profiles of the present invention may include those known to be informative of the state of the immune system in response to infection; however, not all of these biomarkers may be equally informative. These biomarkers can include hormones, autoantibodies, soluble and insoluble receptors, growth factors, transcription factors, cell surface markers and soluble markers from the host or from the pathogen itself, such as coat proteins, lipopolysaccharides (endotoxin), lipoteichoic acids, etc. Other biomarkers include, but are not limited to, cell-surface proteins such as CD64 proteins; CD11b proteins; HLA Class II molecules, including HLA-DR proteins and HLA-DQ proteins; CD54 proteins; CD71 proteins; CD86 proteins; surface-bound tumor necrosis factor receptor (TNF-R); pattern-recognition receptors such as Toll-like receptors; soluble markers such as interleukins IL-1, IL-2, IL-4, IL-6, IL-8, IL-10, IL-11, IL-12, IL-13, and IL-18; tumor necrosis factor alpha (TNF-α); neopterin; C-reactive protein (CRP); procalcitonin (PCT); 6-keto Flα; thromboxane $B_2$; leukotrienes B4, C3, C4, C5, D4 and E4; interferon gamma (IFNγ); interferon alpha/beta (IFN α/β); lymphotoxin alpha (LTα); complement components (C'); platelet activating factor (PAF); bradykinin, nitric oxide (NO); granulocyte macrophage-colony stimulating factor (GM-CSF); macrophage inhibitory factor (MIF); interleukin-1 receptor antagonist (IL-1ra); soluble tumor necrosis factor receptor (sTNFr); soluble interleukin receptors sIL-1r and sIL-2r; transforming growth factor beta (TGFβ); prostaglandin $E_2$ ($PGE_2$); granulocyte-colony stimulating factor (G-CSF); and other inflammatory mediators. (Reviewed in Oberholzer et al., Shock 16: 83-96 (2001) and Vincent et al. in "The Sepsis Text," Carlet et al., eds. (Kluwer Academic Publishers, 2002).) Biomarkers commonly and clinically associated with bacteremia are also candidates for biomarkers useful for the present invention, given the common and frequent occurrence of such biomarkers in biological samples. Biomarkers can include low molecular weight compounds, which can be fragments of proteins or nucleic acids, or they may include metabolites. The presence or concentration of the low molecular weight compounds, such as metabolites, may reflect a phenotypic change that is associated with sepsis and/or SIRS. In particular, changes in the concentration of small molecule biomarkers may be associated with changes in cellular metabolism that result from any of the physiological changes in response to SIRS and/or sepsis, such as hypothermia or hyperthermia, increased heart rate or rate of respiration, tissue hypoxia, metabolic acidosis or MOD. Biomarkers may also include RNA and DNA molecules that encode protein biomarkers.

Biomarkers can also include at least one molecule involved in leukocyte modulation, such as neutrophil activation or monocyte deactivation. Increased expression of CD64 and CD11b is recognized as a sign of neutrophil and monocyte activation. (Reviewed in Oberholzer et al., supra and Vincent et al., supra.) Among those biomarkers that can be useful in the present invention are those that are associated with macrophage lysis products, as can markers of the changes in cytokine metabolism. (See Gagnon et al., Cell 110: 119-31 (2002); Oberholzer, et. al., supra; Vincent, et. al., supra.)

Biomarkers can also include signaling factors known to be involved or discovered to be involved in the inflammatory process. Signaling factors may initiate an intracellular cascade of events, including receptor binding, receptor activation, activation of intracellular kinases, activation of transcription factors, changes in the level of gene transcription and/or translation, and changes in metabolic processes, etc. The signaling molecules and the processes activated by these molecules collectively are defined for the purposes of the present invention as "biomolecules involved in the sepsis pathway." The relevant predictive biomarkers can include biomolecules involved in the sepsis pathway.

Accordingly, while the methods of the present invention may use an unbiased approach to identifying predictive biomarkers, it will be clear to the artisan that specific groups of biomarkers associated with physiological responses or with various signaling pathways may be the subject of particular attention. This is particularly the case where biomarkers from a biological sample are contacted with an array that can be used to measure the amount of various biomarkers through direct and specific interaction with the biomarkers (e.g., an antibody array or a nucleic acid array). In this case, the choice of the components of the array may be based on a suggestion that a particular pathway is relevant to the determination of the status of sepsis or SIRS in an individual. The indication that a particular biomolecule has a feature that is predictive or diagnostic of sepsis or SIRS may give rise to an expectation that other biomolecules that are physiologically regulated in a concerted fashion likewise may provide a predictive or diagnostic feature. The artisan will appreciate, however, that such an expectation may not be realized because of the complexity of biological systems. For example, if the amount of a specific mRNA biomarker were a predictive feature, a concerted change in mRNA expression of another biomarker might not be measurable, if the expression of the other biomarker was regulated at a post-translational level. Further, the mRNA expression level of a biomarker may be affected by multiple converging pathways that may or may not be involved in a physiological response to sepsis.

Biomarkers can be obtained from any biological sample, which can be, by way of example and not of limitation, blood, plasma, saliva, serum, urine, cerebral spinal fluid, sputum, stool, cells and cellular extracts, or other biological fluid sample, tissue sample or tissue biopsy from a host or patient. The precise biological sample that is taken from the individual may vary, but the sampling preferably is minimally invasive and is easily performed by conventional techniques.

Measurement of a phenotypic change may be carried out by any conventional technique. Measurement of body temperature, respiration rate, pulse, blood pressure, or other physiological parameters can be achieved via clinical observation and measurement. Measurements of biomarker molecules may include, for example, measurements that indicate the presence, concentration, expression level, or any other value associated with a biomarker molecule. The form of detection of biomarker molecules typically depends on the method used to form a profile of these biomarkers from a biological sample. For instance, biomarkers separated by 2D-PAGE are detected by Coomassie Blue staining or by silver staining, which are well-established in the art.

Isolation of Useful Biomarkers

It is expected that useful biomarkers will include biomarkers that have not yet been identified or associated with a relevant physiological state. In one aspect of the invention, useful biomarkers are identified as components of a biomarker profile from a biological sample. Such an identification may be made by any well-known procedure in the art, including immunoassay or automated microsequencing.

Once a useful biomarker has been identified, the biomarker may be isolated by one of many well-known isolation procedures. The invention accordingly provides a method of isolating a biomarker that is diagnostic or predictive of sepsis comprising obtaining a reference biomarker profile obtained from a population of individuals, identifying a feature of the reference biomarker profile that is predictive or diagnostic of sepsis or one of the stages in the progression of sepsis, identifying a biomarker that corresponds with that feature, and isolating the biomarker. Once isolated, the biomarker may be used to raise antibodies that bind the biomarker if it is a protein, or it may be used to develop a specific oligonucleotide probe, if it is a nucleic acid, for example.

The skilled artisan will readily appreciate that useful features can be further characterized to determine the molecular structure of the biomarker. Methods for characterizing biomolecules in this fashion are well-known in the art and include high-resolution mass spectrometry, infrared spectrometry, ultraviolet spectrometry and nuclear magnetic resonance. Methods for determining the nucleotide sequence of nucleic acid biomarkers, the amino acid sequence of polypeptide biomarkers, and the composition and sequence of carbohydrate biomarkers also are well-known in the art.

Application of the Present Invention to SIRS Patients

In one embodiment, the presently described methods are used to screen SIRS patients who are particularly at risk for developing sepsis. A biological sample is taken from a SIRS-positive patient, and a profile of biomarkers in the sample is compared to a reference profile from SIRS-positive individuals who eventually progressed to sepsis. Classification of the patient's biomarker profile as corresponding to the reference profile of a SIRS-positive population that progressed to sepsis is diagnostic that the SIRS-positive patient will likewise progress to sepsis. A treatment regimen may then be initiated to forestall or prevent the progression of sepsis.

In another embodiment, the presently described methods are used to confirm a clinical suspicion that a patient has SIRS. In this case, a profile of biomarkers in a sample is compared to reference populations of individuals who have SIRS or who do not have SIRS. Classification of the patient's biomarker profile as corresponding to one population or the other then can be used to diagnose the individual as having SIRS or not having SIRS.

EXAMPLES

The following examples are representative of the embodiments encompassed by the present invention and in no way limit the subject embraced by the present invention.

1.1. Biological Samples Received and Analyzed

Reference biomarker profiles were established for two populations of patient volunteers. The first population ("the SIRS group") represents patients who developed SIRS and who entered into the present study at "Day 1" but who did not progress to sepsis during their hospital stay. The second population ("the sepsis group") represents patients who likewise developed SIRS and entered into the present study at Day 1 but who progressed to sepsis typically at least several days after entering the study. Blood samples were taken about every 24 hours from each study group. Clinical suspicion of sepsis in the sepsis group occurred at "time 0." "Time −24 hours" and "time −48 hours" represent samples taken 24 hours and 48 hours, respectively, preceding the day of clinical suspicion of the onset of sepsis in the sepsis group. That is, the samples from the sepsis group included those taken on the day of entry into the study (Day 1), 48 hours prior to clinical suspicion of sepsis (time −48 hours), 24 hours prior to clinical suspicion of sepsis (time −24 hours), and on the day of clinical suspicion of the onset of sepsis (time 0).

1.2. Analysis of mRNA from the Biological Samples

Whole blood samples isolated from a patient were extracted to remove mRNA using methods known to one of ordinary skill in the art. A suitable RNA isolation procedure is found, for example, in RNA METHODOLOGIES, A LABORATORY GUIDE FOR ISOLATION AND CHARACTERIZATION, 2$^{nd}$ ed., R. E. Farrell, Jr., ed., Academic Press (1998) at pp. 55-104. A filter-based total RNA isolation approach may be used, as described for the use with the RNAqueous™ system (Phenol-Free Total RNA Isolation Kit, Catalog #1912, version 9908; Austin, Tex.). The procedures used for RNA isolation and subsequent manipulations are further described in WO 03/040404, assigned to Source Precision Medicine.

Once isolated, selected RNA species were amplified using message specific primers or random primers. Specific primers were designed from data obtained from public databases, such as Unigene (National Center for Biotechnology Information, National Library of Medicine, Bethesda, Md.). Primers were designed to amplify specific RNA sequences present in the sample using RT-PCR, using principles generally known by one of ordinary skill in the art. (See WO 03/040404, page 22, lines 24-32.) RNA sequences may be amplified using either an isothermic or thermic cycler, such as with an ABI9600, 9700, or 7700 cycler (Applied Biosystems, Foster City, Calif.) Amplified RNAs may then be detected using, for example, fluorescent-tagged detection primers, as described in the TaqMan™ system (PCR Reagent Kit, Protocol, part number 402823, revision A (1996), Applied Biosystems, Foster City, Calif.). RNA detection and quantification may be performed by techniques well-known in the art. (See, e.g., WO 03/040404 at page 23, lines 5-13.)

Following RNA isolation from a patient's blood and purification of the RNA, the following protocol was used to amplify the RNA and react it with a 72-member gene expression array having the nucleic acid probes set forth in TABLE 1:

Materials
1. Applied Biosystems TaqMan Reverse Transcription Reagents Kit (P/N 808-0234). Kit Components: 10× TaqMan RT Buffer, 25 mM Magnesium chloride, deoxyNTP mixture, Random Hexamers, RNase Inhibitor, MultiScribe Reverse Transcriptase (50 U/mL), and RNase/DNase free water (DEPC-Treated Water from Ambion (product number 9915G), or equivalent).

Methods
2. RNA samples were removed from the −80° C. freezer, thawed at room temperature and placed immediately on ice.
3. The following cocktail of Reverse Transcriptase Reagents was prepared for each RT reaction:

|  | per reaction (mL) |
|---|---|
| 10X RT Buffer | 10.0 |
| 25 mM MgCl2 | 22.0 |
| dNTPs | 20.0 |
| Random Hexamers | 5.0 |
| RNAse Inhibitor | 2.0 |
| Reverse Transcriptase | 2.5 |
| Water | 18.5 |
| Total: | 80.0 mL |

4. Each RNA sample was brought up to a total volume of 20 mL in a 1.5 mL microcentrifuge tube and 80 mL RT reaction mix were added. The solution was mixed by pipetting up and down.
5. The sample was incubated at room temperature for 10 minutes.
6. The sample was then incubated at 37° C. for 1 hour.
7. The sample was finally incubated at 90° C. for 10 minutes.
8. The samples were spun for a short time in a microcentrifuge.
9. The samples were then placed on ice if PCR was to be performed immediately. Otherwise, the samples were stored at −20° C. for future use.
10. PCR quality control was run on all RT samples using 18S rRNA and β-actin mRNA as controls.

The use of the primer probe with the first strand cDNA was as described above. Measurement of amplified RNAs that bound to the 72-member gene expression array was performed according to the following procedure:

Materials
1. 20× Primer/Probe Mix for each gene of interest; 20× Primer/Probe Mix for 18S endogenous control; 2× TaqMan Universal PCR Master Mix; cDNA transcribed from RNA extracted from blood samples; Applied Biosystems 96-Well Optical Reaction Plates; Applied Biosystems Optical Caps, or optical-clear film; and Applied Biosystem Prism 7700 Sequence Detector.

Methods
2. Stocks of each Primer/Probe mix were made containing the Primer/Probe for the gene of interest, Primer/Probe for 18S endogenous control, and 2× PCR Master Mix. The following example illustrates a typical set up for one gene with quadruplicate samples testing two conditions (2 plates).

|  | 1X (per well) |
|---|---|
| 2X Master Mix | 12.50 |
| 20X 18S Primer/Probe Mix | 1.25 |
| 20X Gene of interest Primer/Probe Mix | 1.25 |
| Total | 15.00 µL |

3. Stocks of cDNA targets were made by diluting 95 µL of cDNA into 2000 µL of water. The amount of cDNA was adjusted to give Ct values between 10 and 18, typically between 12 and 13.
3. 15 µL of Primer/Probe mix were pipetted into the appropriate wells of an Applied Biosystems 96-Well Optical Reaction Plate.
4. 10 µL of cDNA stock solution were pipetted into each well of the Applied Biosystems 96-Well Optical Reaction Plate.
5. The plate was sealed with Applied Biosystems Optical Caps, or optical-clear film.
6. The plate then was analyzed using an AB Prism 7700 Sequence Detector.

When using a TaqMan format, the number of amplification cycles required to produce a threshold level of fluorescence provides a semi-quantitative estimate of the amount of mRNA corresponding to each gene that was in the sample. When conducted in this fashion, the average coefficient of variation (SD/average×100) of measurement is typically less than 5%, and may be less than 2%. A method of quantifying real-time PCR amplification is described in Hirayama et al., *Blood* 92: 46-52 (1998), for example. Additional aspects of quantitative real-time amplification are described in WO 03/040404 at pages 20-23, for example, and variations of such methods are well-known in the art.

1.3 Data Analysis and Results

For each sample, the concentrations of the mRNAs that bound 72 different cDNA probes on the expression array were measured. In this example, each mRNA is a biomarker, and the concentration of each in the sample can be a feature of that biomarker. The concentration of the biomarkers was determined by their ability to form specific duplexes with the various cDNA probes of the array. The cDNA probes of the array correspond to genes that encode proteins that include various cytokines, chemokines or growth factors, cell markers, proteinases or proteinase inhibitors, receptors, transcription regulators, and enzymes, as shown in TABLE 1. The probes indicated with the asterisks are present on the array described at pages 46-52 of WO 03/040404.

TABLE 1

| Marker | Description | Marker | Description |
|---|---|---|---|
| APAF1 | Apoptotic Protease Activating Factor 1 | IL1A* | Interleukin 1, alpha |
| ARG2 | Extra-Hepatic Arginase | IL1B* | Interleukin 1, beta |
| BPI | Bactericidal/permeability-increasing protein | IL1R1 | Interleukin 1 receptor, type I |
| C1QA* | Complement component 1, q subcomponent, alpha polypeptide | IL1RN* | Interleukin 1 receptor antagonist |
| CALCA | Calcitonin/Calcitonin Gene Related Peptide | IL2* | Interleukin 2 |
| CASP1 | Caspase 1 | IL4* | Interleukin 4 |
| CASP3 | Caspase 3 | IL5* | Interleukin 5 |
| CCL3 | Chemokine (CC-motif) ligand 3 | IL6* | Interleukin 6 (interferon, beta 2) |
| CCR1 | Chemokine (CC-motif) receptor 1 | IL8* | Interleukin 8 |
| CCR3 | Chemokine (CC-motif) receptor 3 | ITGAM | Integrin, Alpha-M |
| CD14* | CD14 antigen | JUN | v-jun avian sarcoma virus 17 oncogene homolog |
| CD19* | CD19 antigen | LBP | Lipopolysaccharide-binding protein |
| CD4* | CD4 antigen | MBL2 | Mannose-binding lectin 2 |
| CD86 | CD86 antigen | MIF | Macrophage Migration Inhibitory Factor |
| CD8A* | CD8 antigen, alpha polypeptide | MMP9* | Matrix metalloproteinase 9 |
| CRP | C-reactive protein | NFKB1 | Nuclear factor of kappa light polypeptide gene enhancer in B-cells 1 (p105) |
| CSF2* | Granulocyte-monocyte colony stimulating factor | NFKBIB | Nuclear factor of kappa light polypeptide gene enhancer in B-cells inhibitor, beta |
| CSF3* | Colony stimulating factor 3 | NOS1 | Nitric oxide synthase 1 (neuronal) |
| CXCL10 | Chemokine (CXC motif) ligand 10 | NOS3 | Nitric oxide-synthase 3 (endothelial) |
| DTR | Diphtheria toxin receptor (heparin-binding epidermal growth factor-like growth factor) | PLA2G7* | Phospholipase A2, group VII (platelet activating factor acetylhydrolase, plasma) |

TABLE 1-continued

| Marker | Description | Marker | Description |
|---|---|---|---|
| ELA2 | Neutrophil elastase | PLAU* | Plasminogen activator, urokinase |
| F3* | Coagulation factor III | SERPINE1* | Serine (or cysteine) protease inhibitor, clade B (ovalbumin), member 1 |
| FCGR1A | Fc fragment of IgG, high affinity IA receptor | SFTPD | Surfactant, pulmonary-associated protein D |
| FTL | Ferritin, light polypeptide | STAT3 | Signal transduction and activator of transcription 3 |
| GZMB | Granzyme B | TGFB1* | Transforming growth factor-beta1 |
| HMOX1* | Heme oxygenase (decycling) 1 | TGFBR2 | Transforming growth factor-beta receptor 2 |
| HSPA1A* | Heat shock protein 70 | TIMP1* | Tissue inhibitor of metalloproteinase 1 |
| ICAM1* | Intercellular adhesion molecule 1 | TLR2 | Toll-like receptor 2 |
| IFI16 | Gamma interferon inducible protein 16 | TLR4 | Toll-like receptor 4 |
| IFNA2* | Interferon, alpha 2 | TNF* | Tumor necrosis factor, alpha |
| IFNG* | Interferon, gamma | TNFRSF13B | Tumor necrosis factor receptor superfamily, member 13b |
| IL10* | Interleukin 10 | TNFSF13B* | Tumor necrosis factor (ligand) superfamily, member 13b |
| IL12B* | Interleukin 12 p40 | TNFSF5* | Tumor necrosis factor (ligand) superfamily, member 6 |
| 1L13* | Interleukin 13 | TNFSF6* | Tumor necrosis factor (ligand) superfamily, member 6 |
| IL18* | Interleukin 18 | TREM1 | Triggering receptor expressed on myeloid cells 1 |
| IL18R1* | Interleukin 18 receptor 1 | VEGF* | Vascular endothelial growth factor |

1.3.1. Cross-Validation

Various approaches may used to identify features that can inform a decision rule to classify individuals into the SIRS or sepsis groups, which are described below. A selection bias can affect the identification of features that inform a decision rule, when the decision rule is based on a large number of features from relatively few biomarker profiles. (See Ambroise et al., *Proc. Nat'l Acad. Sci. USA* 99: 6562-66 (2002).) Selection bias may occur when data are used to select features, and performance then is estimated conditioned on the selected features with no consideration made for the variability in the selection process. The result is an overestimation of the classification accuracy. Without compensation for selection bias, classification accuracies may reach 100%, even when the decision rule is based on random input parameters. (Id.) Selection bias may be avoided by including feature selection in the performance estimation process, whether that performance estimation process is 10-fold cross-validation or a type of bootstrap procedure. (See, e.g., Hastie et al., supra, at 7.10-7.11, herein incorporated by reference.)

In one embodiment of the present invention, model performance is measured by ten-fold cross-validation. Ten-fold cross-validation proceeds by randomly partitioning the data into ten exclusive groups. Each group in turn is excluded, and a model is fitted to the remaining nine groups. The fitted model is applied to the excluded group, and predicted class probabilities are generated. The predicted class probabilities can be compared to the actual class memberships by simply generating predicted classes. For example, if the probability of sepsis is, say, greater than 0.5, the predicted class is sepsis.

Deviance is a measure comparing probabilities with actual outcomes. As used herein, "deviance" is defined as:

$$-2\left\{\sum_{sepsis\ cases} \ln(P(sepsis)) + \sum_{SIRS\ cases} \ln(P(SIRS))\right\}$$

where P is the class probability for the specified class. Deviance is minimized when class probabilities are high for the actual classes. Two models can make the same predictions for given data, yet a preferred model would have a smaller predictive deviance. For each of the ten iterations in the ten-fold cross validation, the predicted deviance is calculated for the cases left out of the model fitting during that iteration. The result is 10 unbiased deviances. Typically, these ten deviances are summed to create a general summary of model performance (i.e., accuracy) on the total data set. Because in fact 10 different models were fit, cross-validation does not prove the performance of a specific model. Rather, the 10 models were generated by a common modeling process, and cross-validation proved the performance of this process. An eleventh model arising from this process will likely have predictive performance similar to those of the first 10. Use of a ten-fold cross-validation typically results in a model performance of less than 100%, but the performance obtained after ten-fold cross-validation is expected to reflect more closely a biologically meaningful predictive accuracy of the decision rule, when applied to biomarker profiles obtained from samples outside of the training set.

1.3.2. Classification Tree Analysis

One approach to analyze this data is to use a classification tree algorithm that searches for patterns and relationships in large datasets. A "classification tree" is a recursive partition to classify a particular patient into a specific class (e.g., sepsis or SIRS) using a series of questions that are designed to accurately place the patient into one of the classes. Each question asks whether a patient's condition satisfies a given predictor, with each answer being used to guide the user down the classification tree until a class into which the patient falls can be determined. As used herein, a "predictor" is a range of values for a feature. In this Example, the feature is a concentration of a nucleic acid biomarker. The nucleic acid biomarkers may be selected from those listed in any one of TABLES 2-10, but the skilled artisan will understand that other nucleic acid biomarkers may be useful for the invention. The "condition" is the single, specific value of the feature that is measured in the individual's biomarker profile. In this example, the "class names" are sepsis and SIRS. Thus, the classification tree user first will ask if a first nucleic acid biomarker concentration measured in the individual's biomarker profile falls within a given range of the first feature's predictive range. The answer to the first question may be dispositive in determining if the individual has SIRS or sepsis. On the other hand, the answer to the first question may further direct the user to ask if a second nucleic acid biomarker concentration measured in the individual's biomarker profile falls within a given range of the second feature's predictive range. Again, the answer to the second question may be dispositive or may direct the user further down the classification tree until a patient classification is ultimately determined.

1.3.3. Multiple Additive Regression Trees

An automated, flexible modeling technique that uses multiple additive regression trees (MART) was used to classify sets of features as belonging to one of two populations. A MART model uses an initial offset, which specifies a constant that applies to all predictions, followed by a series of regression trees. Its fitting is specified by the number of decision points in each tree, the number of trees to fit, and a "granularity constant" that specifies how radically a particular tree can influence the MART model. For each iteration, a regression tree is fitted to estimate the direction of steepest descent of the fitting criterion. A step having a length specified by the granularity constant is taken in that direction. The MART model then consists of the initial offset plus the step provided by the regression tree. The differences between the observed and predicted values are recalculated, and the cycle proceeds again, leading to a progressive refinement of the prediction. The process continues either for a predetermined number of cycles or until some stopping rule is triggered.

The number of splits in each tree is a particularly meaningful fitting parameter. If each tree has only one split, the model looks only at one feature and has no capability for combining two predictors. If each tree has two splits, the model can accommodate two-way interactions among features. With three trees, the model can accommodate three-way interactions, and so forth.

The value of sets of features in predicting class status was determined for data sets with features and known class status (e.g., sepsis or SIRS). MART provides a measure of the contribution or importance of individual features to the classification decision rule. Specifically, the degree to which a single feature contributes to the decision rule upon its selection at a given tree split can be measured to provide a ranking of features by their importance in determining the final decision rule. Repeating the MART analysis on the same data set may yield a slightly different ranking of features, especially with respect to those features that are less important in establishing the decision rule. Sets of predictive features and their corresponding biomarkers useful in the present invention thus may vary slightly from those set forth herein.

One implementation of the MART technology is found in a module, or "package," for the R statistical programming environment (see Venables et al., in *Modern Applied Statistics with S*, 4$^{th}$ ed. (Springer, 2002); www.r-project.org). Results reported in this document were calculated using R versions 1.7.0 and 1.7.1. The module implementing MART, written by Dr. Greg Ridgeway, is called "gbm" and is also freely available for download (see www.r-project.org). The MART algorithm is amenable to ten-fold cross-validation. The granularity parameter was set to 0.05, and the gbm package's internal stopping rule was based on leaving out 20% of the data cases at each marked iteration. The degree of interaction was set to one, so no interactions among features were considered. The gbm package estimates the relative importance of each feature on a percentage basis, which cumulatively equals 100% for all the features of the biomarker profile. The features with highest importance, which together account for at least 90% of total importance, are reported as potentially having predictive value. Note that the stopping rule in the fitting of every MART model contributes a stochastic component to model fitting and feature selection. Consequently, multiple MART modeling runs based on the same data may choose slightly, or possibly even completely, different sets of features. Such different sets convey the same predictive information; therefore, all the sets are useful in the present invention. Fitting MART models a sufficient number of times is expected to produce all the possible sets of predictive features within a biomarker profile. Accordingly, the disclosed sets of predictors are merely representative of those sets of features that can be used to classify individuals into populations.

Data from nucleic acid biomarker profiles obtained from various samples were analyzed using MART, as described above. In this analysis, the time 0 hours sepsis population consisted of 23 patients and the SIRS population consisted of 24 patients, while the time −24 hours and time −48 hours populations consisted of 24 and 21 individuals with sepsis and SIRS, respectively. Features corresponding to all 72 of the biomarkers listed in TABLE 1 were analyzed.

For the time 0 hours populations, the fitted model included 23 trees, and the model allowed no interactions among the features. Using ten-fold cross-validation, the model correctly classified 19 of 24 SIRS patients and 15 of 23 sepsis patients, giving a model sensitivity of 65% and a specificity of 79%. The biomarkers are ranked in order of importance, as determined by the model, in TABLE 2. All features with zero importance are excluded. Markers indicated with a sign of "−1" were expressed at progressively higher levels in sepsis-positive populations as sepsis progressed, while those biomarkers with a sign of "1" were expressed at progressively lower levels.

TABLE 2 feature importance by MART analysis: time 0 hours samples

| | Biomarker | Importance | Sign |
|---|---|---|---|
| 1 | FCGR1A | 23.769 | −1 |
| 2 | ARG2 | 20.121 | −1 |
| 3 | CD86 | 19.466 | 1 |
| 4 | IL18R1 | 10.190 | −1 |
| 5 | MMP9 | 9.1892 | −1 |
| 6 | CD4 | 9.0302 | 1 |
| 7 | IL1B | 4.7283 | −1 |
| 8 | IL8 | 1.9926 | 1 |
| 9 | IL4 | 1.5133 | −1 |

For the time −24 hours populations, the fitted model included 12 trees, and the model allowed no interactions among the features. Using ten-fold cross-validation, the model correctly classified 15 of 21 SIRS patients and 17 of 24 sepsis patients, giving a model sensitivity of 71% and a specificity of 71%. The biomarkers are ranked in order of importance, as determined by the model, in TABLE 3.

TABLE 3 feature importance by MART analysis: time −24 hours samples

| | Biomarker | Importance | Sign |
|---|---|---|---|
| 1 | FCGR1A | 60.650 | −1 |
| 2 | ARG2 | 15.188 | −1 |
| 3 | CD4 | 7.3189 | 1 |
| 4 | IL8 | 6.0636 | 1 |
| 5 | TLR4 | 5.3904 | −1 |
| 6 | CSF2 | 5.3896 | 1 |

For the time −48 hours populations, the fitted model included nine trees, and the model allowed no interactions among the features. Using ten-fold cross-validation, the model correctly classified 8 of 21 SIRS patients and 20 of 24 sepsis patients, giving a model sensitivity of 83%, a specificity of 38%, and an accuracy of 62%. The biomarkers are ranked in order of importance, as determined by the model, in TABLE 4.

TABLE 4 feature importance by MART analysis: time -48 hours samples

| | Biomarker | Importance | Sign |
|---|---|---|---|
| 1 | CD4 | 49.232 | 1 |
| 2 | ARG2 | 18.450 | −1 |
| 3 | MMP9 | 13.778 | −1 |
| 4 | HSPA1A | 10.662 | −1 |
| 5 | LBP | 7.8786 | 1 |

1.3.4. Logistic Regression Analysis

Logistic regression provides yet another means of analyzing a data stream from the analysis described above. "Signal intensity" is equivalent to a concentration of a particular nucleic acid biomarker. The absence of a signal for a given nucleic acid biomarker results in an assigned signal intensity of "0." The standard deviations (SD) of the signal intensities from a given nucleic acid biomarker are then obtained from the profiles of the combined SIRS and sepsis populations. If there is no variation in signal intensity between SIRS and sepsis populations (i.e., the SD=0), the signal intensity is not considered further. Before regression analysis, signal intensities are scaled, using methods well known in the art. Scaling algorithms are generally described in Hastie et al., supra, at Chapter 11.

1.3.5. Wilcoxon Signed Rank Test Analysis

In yet another method, a nonparametric test such as a Wilcoxon Signed Rank Test can be used to identify individual biomarkers of interest. The features in a biomarker profile are assigned a "p-value," which indicates the degree of certainty with which the biomarker can be used to classify individuals as belonging to a particular reference population. Generally, a p-value having predictive value is lower than about 0.05. Biomarkers having a low p-value can be used by themselves to classify individuals. Alternatively, combinations of two or more biomarkers can be used to classify individuals, where the combinations are chosen on the basis of the relative p-value of a biomarker. In general, those biomarkers with lower p-values are preferred for a given combination of biomarkers. Combinations of at least three, four, five, six, 10, 20 or 30 or more biomarkers also can be used to classify individuals in this manner. The artisan will understand that the relative p-value of any given biomarker may vary, depending on the size of the reference population.

Using the Wilcoxon Signed Rank Test, biomarkers that formed specific duplexes with (i.e., hybridized to) an expression array having the probes listed in TABLE 1 were assigned a p-value by comparison of sepsis and SIRS populations at a given time. That is, p-values were assigned to features from biomarker profiles obtained from biological samples taken at time 0 hours, time −24 hours, and time −48 hours. These p-values are listed in TABLES 5, 6 and 7, respectively. For this analysis, the sepsis and SIRS populations at time 0 (TABLE 5) constituted 23 and 24 patients, respectively; and the sepsis and SIRS populations at time −24 hours and time −48 hours (TABLES 6 and 7) constituted 24 and 21 patients, respectively.

TABLE 5 p-values for features: time 0 hours

| | Biomarker | P-Value |
|---|---|---|
| 1 | FCGR1A | 2.2792e−06 |
| 2 | CD4 | 6.1183e−06 |
| 3 | IL18R1 | 3.0476e−05 |
| 4 | CD86 | 8.8376e−05 |
| 5 | ARG2 | 2.3979e−04 |
| 6 | IL1RN | 3.8982e−04 |
| 7 | MMP9 | 5.1390e−04 |
| 8 | PLA2G7 | 7.1485e−04 |
| 9 | ITGAM | 8.6695e−04 |
| 10 | TNFSF5 | 9.2451e−04 |
| 11 | HSPA1A | 2.4353e−03 |
| 12 | TLR4 | 3.6131e−03 |
| 13 | TNFSF13B | 3.6140e−03 |
| 14 | NOS3 | 4.0315e−03 |
| 15 | IL10 | 4.8175e−03 |
| 16 | CCR1 | 5.1829e−03 |
| 17 | IFI16 | 5.4665e−03 |
| 18 | TNFSF6 | 6.1913e−03 |
| 19 | TIMP1 | 7.3280e−03 |
| 20 | IL1R1 | 8.8140e−03 |
| 21 | GFB1 | 1.1998e−02 |
| 22 | IL1B | 1.7946e−02 |
| 23 | ICAM1 | 2.7022e−02 |
| 24 | CD8A | 2.9415e−02 |
| 25 | TLR2 | 3.3769e−02 |
| 26 | CCR3 | 3.7145e−02 |
| 27 | TGFBR2 | 3.9687e−02 |
| 28 | SERPINE1 | 4.3568e−02 |

TABLE 6 p-values for features: time -24 hours

| | Biomarker | P-Value |
|---|---|---|
| 1 | FCGR1A | 3.9756e−06 |
| 2 | CD4 | 1.4742e−03 |
| 3 | IL18R1 | 1.6002e−03 |
| 4 | IL10 | 6.5097e−03 |
| 5 | PLA2G7 | 8.1124e−03 |
| 6 | ARG2 | 8.6978e−03 |
| 7 | TIMP1 | 9.0121e−03 |
| 8 | TNFSF13B | 1.0058e−02 |
| 9 | TLR4 | 1.5071e−02 |
| 10 | CCR1 | 1.7184e−02 |
| 11 | IL1RN | 2.1489e−02 |
| 12 | ITGAM | 3.0112e−02 |
| 13 | IL1R1 | 3.1000e−02 |
| 14 | MMP9 | 3.3894e−02 |
| 15 | TNFSF5 | 4.7616e−02 |

TABLE 7 p-values for features: time -48 hours

| | Biomarker | P-Value |
|---|---|---|
| 1 | CD4 | 3.2310e−04 |
| 2 | IL18R1 | 2.1669e−03 |
| 3 | ARG2 | 2.6612e−03 |
| 4 | TIMP1 | 7.8084e−03 |
| 5 | MMP9 | 1.0743e−02 |
| 6 | PLA2G7 | 1.1513e−02 |
| 7 | FCGR1A | 1.2753e−02 |
| 8 | TNFSF6 | 2.5873e−02 |
| 9 | IL1R1 | 4.0306e−02 |
| 10 | BPI | 4.1490e−02 |

A nonparametric test (e.g., a Wilcoxon Signed Rank Test) alternatively can be used to find p-values for features that are based on the progressive appearance or disappearance of the feature in populations that are progressing toward sepsis. In this form of the test, a baseline value for a given feature first is measured, using the data from the time of entry into the study (Day 1 samples) for the sepsis and SIRS groups. The feature intensity in sepsis and SIRS samples is then compared in, for example, time −48 hour samples, to determine whether the feature intensity has increased or decreased from its baseline value. Finally, p-values are assigned to the difference from baseline in a feature intensity in the sepsis populations versus the SIRS populations. The following p-values, listed in TABLES 8-10, were obtained when measuring these differences from baseline in p-values.

TABLE 8 p-values for features differenced from baseline: time 0 hours

| | Biomarker | P-Value |
|---|---|---|
| 1 | FCGR1A | 2.6701e−05 |
| 2 | IL1RN | 1.6453e−03 |
| 3 | IL18R1 | 3.2954e−03 |
| 4 | MMP9 | 5.5538e−03 |
| 5 | ITGAM | 5.8626e−03 |
| 6 | IL1B | 8.3804e−03 |
| 7 | TLR2 | 8.9614e−03 |
| 8 | TLR4 | 9.8975e−03 |
| 9 | CD4 | 1.1616e−02 |
| 10 | CCR1 | 1.1619e−02 |
| 11 | TNFSF13B | 1.2183e−02 |
| 12 | PLA2G7 | 1.3831e−02 |
| 13 | CD86 | 1.7683e−02 |
| 14 | IL10 | 2.8201e−02 |
| 15 | CCR3 | 3.3319e−02 |
| 16 | ICAM1 | 3.3319e−02 |

TABLE 9 p-values for features differenced from baseline: time −24 hours

| | Biomarker | P-Value |
|---|---|---|
| 1 | FCGR1A | 2.3809e−04 |
| 2 | IL18R1 | 1.7692e−02 |
| 3 | SFTPD | 2.3309e−02 |
| 4 | TLR4 | 3.0107e−02 |
| 5 | TNFSF13B | 4.3896e−02 |

TABLE 10 p-values for features differenced from baseline: time −48 hours

| | Biomarker | P-Value |
|---|---|---|
| 1 | ARG2 | 1.2741e−02 |
| 2 | LBP | 3.8573e−02 |

Having now fully described the invention with reference to certain representative embodiments and details, it will be apparent to one of ordinary skill in the art that changes and modifications can be made thereto without departing from the spirit or scope of the invention as set forth herein.

What is claimed is:

1. A method of predicting an increased likelihood of developing sepsis in a human SIRS patient comprising:

determining abundances of Fc fragment of IgG, high affinity 1A receptor (FCGR1A) mRNA and extra-hepatic arginase (ARG2) mRNA in a first blood sample taken from the human SIRS patient; and comparing the abundances of FCGR1A and ARG2 mRNAs in the first blood sample to abundances of FCGR1A and ARG2 mRNAs in blood samples taken 0-48 hours prior to sepsis in a SIRS-positive human patient population that progresses to sepsis, wherein the abundances of FCGR1A and ARG2 mRNAs in the blood samples taken from the SIRS-positive human patient population that progresses to sepsis are statistically significantly greater than abundances of FCGR1A and ARG2 mRNAs in blood samples taken from a SIRS-positive human patient population that does not progress to sepsis, and wherein an increased likelihood of developing sepsis is predicted in the SIRS patient when it is determined that the FCGR1A and ARG2 mRNA abundances in the first blood sample are statistically significantly similar to the abundances of FCGR1A and ARG2 mRNAs in the blood samples taken from the SIRS-positive human patient population that progresses to sepsis, and wherein the SIRS-positive patient population that progresses to sepsis and the SIRS-positive human patient population that does not progress to sepsis each comprise at least 20 individuals.

2. The method of claim 1, wherein the comparison comprises applying a decision rule.

3. The method of claim 2, wherein applying the decision rule comprises using a data analysis algorithm.

4. The method of claim 3, wherein the data analysis algorithm comprises the use of a classification tree.

5. The method of claim 3, wherein the data analysis algorithm is nonparametric.

6. The method of claim 5, wherein the data analysis algorithm detects differences in a distribution of feature values.

7. The method of claim 6, wherein the nonparametric algorithm comprises using a Wilcoxon Signed Rank Test.

8. The method of claim 3, wherein the data analysis algorithm comprises using a multiple additive regression tree.

9. The method of claim 3, wherein the data analysis algorithm is a logistic regression.

10. The method of claim 3, wherein the data analysis algorithm comprises at least two input parameters.

11. The method of claim 10, wherein the data analysis algorithm comprises at least five input parameters.

12. The method of claim 11, wherein the data analysis algorithm comprises at least ten input parameters.

13. The method of claim 12, wherein the data analysis algorithm comprises at least twenty input parameters.

14. The method of claim 1, wherein the blood samples from the SIRS-positive patient population that progresses to sepsis are taken within about 48 hours prior to sepsis.

15. The method of claim 1, wherein the blood samples from the SIRS-positive patient population that progresses to sepsis are taken within about 24 hours prior to sepsis.

16. The method of claim 1, wherein the comparison predicts sepsis in the SIRS patient with an accuracy of at least 60%.

17. The method of claim 16, wherein the comparison predicts sepsis in the SIRS patient with an accuracy of at least 70%.

18. The method of claim 16, wherein the comparison predicts sepsis in the SIRS patient with a sensitivity of at least 60%.

19. The method of claim 1 further comprising comparing the abundances of FCGR1A and ARG2 mRNAs in the first blood sample to abundances of FCGR1A and ARG2 mRNAs in blood samples taken from a SIRS-positive patient population that does not progress to sepsis.

20. The method of claim 1 further comprising
determining abundances of one or more nucleic acids in the first blood sample, wherein the one or more nucleic acids are mRNAs selected from the group consisting of CD86 antigen (CD86) mRNA; interleukin 18 receptor 1 (IL18R1) mRNA; matrix metalloproteinase 9 (MMP9) mRNA; CD4 antigen (CD4) mRNA; interleukine 1, beta (IL1B) mRNA; interleukin 8 (IL8) mRNA; interleukin 4 (IL4) mRNA; toll-like receptor 4 (TLR4) mRNA; granulocyte-monocyte colony stimulating factor (CSF2) mRNA; heat shock protein 70 (HSPA1A) mRNA; lipopolysaccharide-binding protein (LBP) mRNA; interleukin 1 receptor antagonist (IL1RN) mRNA; phospholipase A2, group VII (platelet activating factor acetylhydrolase, plasma) (PLA2G7) mRNA; integrin, alpha-M (ITGAM) mRNA; tumor necrosis factor (ligand) superfamily, member 5 (TNFSF5) mRNA; tumor necrosis factor (ligand) superfamily, member 13b (TNFSF13B) mRNA; nitric oxide-synthase 3 (NOS3) mRNA; interleukin 10 (IL10) mRNA; chemokine (CC-motif) receptor 1 (CCR1) mRNA; gamma interferon inducible protein 16 (IFI16) mRNA; tumor necrosis factor (ligand) superfamily, member 6 (TNFSF6) mRNA; tissue inhibitor of metalloproteinase 1 (TIMP1) mRNA; interleukin 1 receptor, type 1 (IL1R1) mRNA; transforming growth factor-beta1 (TGFB1) mRNA; intercellular adhesion molecule 1 (ICAM1) mRNA; CD8 antigen, alpha polypeptide (CD8A) mRNA; toll-like receptor 2 (TLR2) mRNA; chemokine (CC-motif) receptor 3 (CCR3) mRNA; transforming growth factor-beta receptor 2 (TGFBR2) mRNA; serine (or cysteine) protease inhibitor, clade B (ovalbumin), member 1 (SERPINE1) mRNA; bactericidal/permeability-increasing protein (BPI) mRNA; and surfactant, pulmonary-associated protein D (SFTPD) mRNA; and
comparing the abundances of the one or more nucleic acids in the first blood sample to abundances of the one or more nucleic acids in blood samples taken 0-48 hours prior to sepsis in a SIRS-positive human patient population that progresses to sepsis.

21. The method of claim 20, wherein the one or more nucleic acids comprise at least five mRNAs.

22. The method of claim 14, wherein the abundances of FCGR1A and ARG2 mRNAs in the first blood sample are determined by hybridizing FCGR1A and AGR2 mRNAs to an array comprising oligonucleotides or cDNAs.

23. The method of claim 1, wherein the abundances of FCGR1A and ARG2 mRNAs in the first blood sample are determined by reverse transcription of mRNAs in the first blood sample and amplification and detection of FCGR1A and ARG2 cDNAs.

24. The method of claim 1, wherein the compared abundances of FCGR1A and ARG2 mRNAs in the first blood sample and in the blood samples taken from the SIRS-positive patient population that progresses to sepsis are relative to abundances of an internal control nucleic acid.

25. The method of claim 24, wherein the internal control nucleic acid is 18S rRNA or β-actin mRNA.

26. The method of claim 1, further comprising isolating the first blood sample from the human SIRS patient.

27. The method of claim 1, wherein said comparing step is performed on a computer, the method further comprising reporting a result of the comparing step to a clinician.

* * * * *

UNITED STATES PATENT AND TRADEMARK OFFICE
CERTIFICATE OF CORRECTION

PATENT NO. : 7,645,573 B2
APPLICATION NO. : 10/704666
DATED : January 12, 2010
INVENTOR(S) : Ivey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 842 days.

Signed and Sealed this

Sixteenth Day of November, 2010

David J. Kappos
*Director of the United States Patent and Trademark Office*